(12) United States Patent
Burke et al.

(10) Patent No.: US 6,897,200 B1
(45) Date of Patent: May 24, 2005

(54) OLIGONUCLEOTIDE DELIVERY SYSTEMS FOR CAMPTOTHECINS

(75) Inventors: Thomas G. Burke, Lexington, KY (US); Ayhan S. Demir, Lexington, KY (US); Ashok J. Chavan, Lexington, KY (US); Danzhou Yang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/807,332

(22) PCT Filed: Oct. 14, 1998

(86) PCT No.: PCT/US98/20941
§ 371 (c)(1),
(2), (4) Date: May 21, 2001

(87) PCT Pub. No.: WO00/21370
PCT Pub. Date: Apr. 20, 2000

(51) Int. Cl.[7] .................. A61K 48/00; C07D 491/22
(52) U.S. Cl. .................. 514/44; 514/23.1; 546/48
(58) Field of Search .................. 514/44, 23.1, 283; 546/48; 424/450, 93.2; 435/320.1

(56) References Cited

U.S. PATENT DOCUMENTS

| | | |
|---|---|---|
| 5,276,019 A | 1/1994 | Cohen et al. |
| 5,447,936 A | 9/1995 | Hausheer et al. |
| 5,552,156 A | 9/1996 | Burke |
| 5,583,034 A | * 12/1996 | Green .................. 435/325 |
| 5,604,233 A | 2/1997 | Hausheer et al. |
| 5,651,986 A | 7/1997 | Brem et al. |
| 5,674,873 A | 10/1997 | Hausheer et al. |
| 5,677,286 A | 10/1997 | Shull et al. |
| 5,714,170 A | 2/1998 | Baserga et al. |
| 5,726,181 A | 3/1998 | Hausheer et al. |
| 5,736,156 A | 4/1998 | Burke |
| 5,834,012 A | * 11/1998 | Perez-Soler et al. ........ 424/450 |
| 6,407,117 B1 | * 6/2002 | Bouscarel et al. .......... 514/283 |

OTHER PUBLICATIONS

Verma, Nature, vol. 389, 1997, 239–242.*
Pantazis, J. Biomedical Science, 6, 1, 1–7, 1999.*
Yang et al., J. Am. Chem. Soc. 120, 2979–2980, Published on Web, Mar. 12, 1998.*
Chourpa (Specgtroscopy of Bviological Molecules: Modern Trends, [European Conferenceon Spectroscopy of Biological Molecules], 7th, Madrid, 1997.*

Matteucci (J. Am. Chem. Soc. 1997, vol. 119, 6939–6940).*

Schaack et al., J. Virology, vol. 64, No. 1, 78–85, 1990.*

Jaxel et al., Effect of Local DNA sequence on Topoisomerase I Cleavage in the Presence or Absense of Camptothecin. The Journal of Biological Chemistry. Oct. 25, 1991, vol. 266, No. 30, pp. 20418–20423, especially the abstract.

Database Caplus on STN, AN 1997:725569, Fleury et al. Conformation and mechanism in DNA–topoisomerase I as a target of antitumor drugs: optical spectroscopy approach. Spectrosc. Biol. Mol.; Mod. Trends. 1997, Eur. Conf. 7th, Conference Abstct.

Leteurtre et al. Specific Interaction of Camptothecin, a Topoisomerase I Inhibitor, with Guanine Residues of DNA detected by Photoactivation at 365 nm. Biochemistry. 1993, vol. 32, pp. 8955–8962, especially abstract.

Giovanella, et al., DNA Topoisomerase I–Targeted Chemotherapy of Human Colon Cancer in Xenografts, Science 246: 1046–1048 (Washington, DC) (1989).

Madden, T.D., Burke, T.G., Redelmeier, T.E. and Bally, M.B., "Encapsulation of Topotecan in Lipid–Based Carriers: Evaluation of Drug Stability and Plasma Elimination in a Murine Model", Proc. Am. Soc. Clin. Oncol., 17: 196a (1998).

* cited by examiner

*Primary Examiner*—Dave Trong Nguyen
(74) *Attorney, Agent, or Firm*—King & Schickli, PLLC

(57) ABSTRACT

Camptothecin drugs are stabilized in their antitumor active lactone form by complexation with an oligonucleotide including RNA or catalytic RNA. The oligonucleotide-camptothecin drug complex may be incorporated within a macromolecular assembly including both viral and non-viral oligonucleotide vectors. The invention allows combination gene and camptothecin drug therapy.

11 Claims, 9 Drawing Sheets

Stability of CPT-11 and TPT Lactone Form in the Absence and Presence of DNA in PBS 7.4 at Room Temperature

OLIGONUCLEOTIDE DELIVERY SYSTEMS FOR CAMPTOTHECINS

This is a National Stage Application under 35 U.S.C. §371 of International Application No. PCT/US98/20941, filed on Oct. 14, 1998.

This invention was made with Government support under NIH grant NIH CA: 63653. The Government may have certain rights in this invention.

TECHNICAL FIELD

The present invention relates generally to camptothecin anticancer drugs and the use of oligonucleotides to bind selectively the lactone forms of camptothecins, thereby conserving the agents in their biologically active lactone forms.

BACKGROUND OF THE INVENTION

Camptothecin, a plant alkaloid isolated from trees indigenous to China, and analogues thereof such as 9-aminocamptothecin, 9-nitrocamptothecin, 10-hydroxycamptothecin, 10,11-methylenedioxycamptothecin, 9-nitro-10,11-methylenedioxycamptothecin, 9-chloro-10,11-methylenedioxycamptothecin, 9-amino-10,11-methylenedioxycamptothecin, 7-ethyl-10-hydroxycamptothecin (SN-38), topotecan, DX-8951, GG211, 7-trimethylsilylmethylcamptothecin, and other analogues (collectively referred to herein as camptothecin drugs) are presently under study worldwide in research laboratories and cancer clinics. In lab tests and in clinical trials, these camptothecin drugs have aroused considerable interest as a result of their ability to halt the growth of a wide range of human tumors. For example, these drugs exhibit unprecedented high levels of antitumor activities against human colon cancer [Giovanella, et al. *Science* 246: 1046–1048 (Wash. D.C.) (1989)]. Camptothecin has also been shown to be effective against other experimental cancer types such as lung, breast, and malignant melanoma.

Camptothecin is thought to inhibit the proliferation of cancer cells by interfering with the breakage/reunion reaction of the enzyme topoisomerase I, a nuclear enzyme implicated in DNA replication and RNA transcription. A camptothecin drug stabilizes and forms a reversible enzyme-camptothecin-DNA ternary complex, designated the cleavage complex. The formation of the cleavable complex specifically prevents the reunion step of the breakage/union cycle of the topoisomerase reaction.

However, the clinical use of the camptothecin drugs is limited by their chemical properties. First, the camptothecin drugs are insoluble in water which hinders the delivery of the drug to the cancer cells. Second, the camptothecin drugs are extremely susceptible to hydrolysis; in an aqueous environment such as blood plasma, the half life is about 16 to 20 minutes and active lactone concentrations can fall to almost negligible levels depending upon the analogue. The camptothecin drugs each contain a substituted quinoline nucleus (rings A–C) and, at the opposite end an α-hydroxy lactone ring which is very unstable in aqueous environments. In blood plasma the ring is quickly opened to create the carboxylate form of the drug, which is poorly accumulated by cancer cells. Once internalized by the cancer cells, the carboxylate form exhibits no activity against its molecular target, topoisomerase I. Thus, the hydrolyzed product is ineffective at treating cancer. Moreover, the hydrolyzed product appears to be more toxic to healthy tissue than the camptothecin drugs.

Numerous attempts have, of course, been made to address these problems and shortcomings. To date, one of the most successful ways for maintaining camptothecin drugs in the antitumor-active lactone form is by stabilization of the drug in macromolecular lipid or surfactant assemblies such as liposomes or micelles, The liposomal or micellular stabilization of camptothecins is described in detail in U.S. Pat. Nos. 5,552,156 and 5,736,156 both to Burke. Specifically, the lactone ring of the camptothecin drugs is stabilized in the membrane of the vesicles. Typically, the camptothecin drugs bind the lipid bilayer membrane of the liposome and the surfactant monolayer membrane of the micelles. The liposome-bound or micelle-bound drug is protected from hydrolysis, thus preserving the antitumor activity of the drug.

The liposome is comprised of lipids such as, for example, phospholipids or cholesterol. For the camptothecin drugs which have a lower affinity for the liposome membrane and thus disassociate from the liposomal membrane to reside in the interior of liposome, the pH of the internal environment of the liposome is reduced thereby preventing hydrolysis of the camptothecin drug. Camptothecin drugs are also stabilized by association with micelles comprised of surfactants such as sodium dodecylsulfate (SDS), octylphenolpolyoxyethylene glycol and sorbitan mono-oleate.

Recently the effectiveness of liposomal topotecan formulations were evaluated in animal models. Although topotecan exhibits good clinical activity against a variety of tumor types, it undergoes rapid hydrolysis in vivo from the active, lactone species to the inactive carboxylate. This inactivation, coupled with cell-cycle-specific behavior and fairly rapid elimination, results in highly schedule-dependent clinical activity. Liposomal carriers accumulate selectively at tumor sites and can potentially act as sustained release systems maintaining therapeutic drug levels over a prolonged period. In the case of topotecan, such carriers might also protect the drug in its lactone form until released. A procedure whereby topotecan could be efficiently encapsulated within lipid-based carriers employing an ion gradient loading procedure and delivered to tumors has been developed (Madden et al., 1998). In contrast to earlier studies on liposomal delivery in which camptothecins were inserted predominantly into the lipid bilayer, the current technique entraps topotecan in the aqueous core of the carrier. Drug uptake was rapid (approximately 60 min. at 60° C.) and high encapsulation efficiencies (>95%) were readily achieved at relatively high drug:lipid ratios (0.1:1 mole ratio). Plasma elimination rates were compared for free topotecan and encapsulated drug (liposomal topotecan) in mice. Following a bolus intravenous injection (lateral tail vein) at 10 mg/kg, plasma level were followed for up to 24 hours. Plasma levels of topotecan given in the liposomal formulation were approximately two orders of magnitude higher than for free drug over this timecourse. Further, by employing carriers with an acidic interior the entrapped topotecan was protected as the lactone species (85% lactone at 24 hours). Antitumor efficacy was compared for free and liposomal topotecan in the murine L1210 model (i.p. tumor inoculation/i.v. treatment) using either a single bolus injection on day 1 (10 or 20 mg/kg), or bolus injections on days 1, 5, 9 (4 or 8 mg/kg). In all treatment schedules liposomal topotecan exhibited much greater antitumor activity than did free drug.

While the liposomal and micellar stabilization of camptothecin drugs described in U.S. Pat. Nos. 5,552,156 and 5,736,176 to Burke address and effectively overcome the instability and insolubility problems of camptothecin drugs administered in their free form, further improvements leading to more efficient, diversified and effective administration and treatment of tumors and various cancer types are still possible and are actively being sought.

Toward that end, we have developed the present invention. Specifically, we have found that direct noncovalent binding interactions of camptothecin drugs with oligonucleotides conserve the active forms of the drugs (i.e. the active lactone forms of camptothecin drugs are found to be stable when complexed with oligonucleotides). The oligonucleotides include single-stranded DNA, double-stranded DNA, antisense DNA, RNA, and catalytic RNA. The invention describes macromolecular assemblies which include both viral or non-viral oligonucleotide vectors. The viral gene delivery systems include retroviruses, adenoviruses, adeno-associated viruses, Herpes viruses, Vaccinia viruses, and other virus particles. The non-viral delivery systems include transfection vehicles, naked DNA for injection, gene gun particles, liposomes including cationic liposomes, virosomes, receptor-mediated delivery vehicles, and biodegradable and non-biodegradable polymer matrixes. The macromolecular assemblies can consist of the following materials: biodegradable and non-biodegradable polymers, lipids, carbohydrates, proteins and biologically relevant molecules which facilitate the delivery, accumulation and processing of the oligonucleotides and drugs to target tissues within the human body. Each of the above oligonucleotide delivery vectors contain oligonucleotides which act to stabilize the lactone forms of camptothecin drugs. The oligonucleotide contained within the vectors can serve as a stabilizing matrix for the drug and the stabilization can be effective over a wide pH range, the vectors also provide a means for the controlled, targeted and stable delivery of camptothecin drug to target tissue. In addition to stabilizing camptothecin, the oligonucleotides carried in the vectors serve an additional role in exerting gene therapy or pharmacological effects in general which can be envisioned to augment the effects of camptothecins on the host target tissue and the patient receiving the therapy. The combination of stable camptothecin drug delivery and gene therapy can have potentially unique and desirable consequences on inhibiting the spread of cancer and other disease states in humans and animals.

SUMMARY OF THE INVENTION

Accordingly, it is a primary object of the present invention to provide stable, water soluble, highly pharmacologically active camptothecin drugs overcoming the above described limitations and disadvantages of the prior art including the instability and insolubility problems of camptothecin drugs administered in free form.

Still another object of the present invention is to provide camptothecin drugs formed in complex with an oligonucleotide including DNA and RNA wherein the formation of the complex results in binding interactions between the active lactone form of the drug and the oligonucleotide.

The prior art concerning camptothecin interactions with DNA indicated that there was only very limited direct experimental evidence that camptothecin and its analogs/derivatives bind to oligonucleotides such as DNA in the absence of the t+opoisomerase I protein. Earlier work suggests that camptothecin derivatives bind to neither isolated DNA structures nor isolated topoisomerase I; the researchers indicated that the drug only binds to the DNA-topoisomerase 1 complex (Hertzberg et al., *J. Biol. Chem.* 265: 19287–19295 (1990)). Other studies have suggested that camptothecin drugs may weakly interact with intact dsDNA, but no effect on the active lactone drug concentrations were reported (Fukada et al., *Biochemical Pharmacology* 34: 1225–1230 (1985); Leteurtre et al., *Biochemistry* 32: 8955–8963 (1993)). Until we completed our studies it was not known that camptothecins can bind to DNA and these interactions act to conserve the active lactone forms of these medications (Yang et al. *J. Am. Chem. Soc.* 120: 2979–2980 (1998).

The present invention relates generally to camptothecin anticancer drugs and the use of oligonucleotides to bind selectively the lactone forms of camptothecin drugs. The binding interactions act to conserve the agents in their biologically-active lactone forms. Direct noncovalent binding interactions of a camptothecin drug of SN-38 lactone with oligonucleotide is described here. The interactions are found to conserve the active forms of the drugs (i.e. the active lactone forms of camptothecins are found to be stable when complexed with oligonucleotides).

The oligonucleotides include single-stranded DNA, double-stranded DNA, antisense DNA, RNA, and catalytic RNA, among others. This invention describes macromolecular assemblies which include both viral or non-viral oligonucleotide vectors. The viral gene delivery systems include retroviruses, adenoviruses, adeno-associated viruses, Herpes viruses, Vaccinia viruses, and other virus particles. The non-viral delivery systems include transfection vehicles, naked DNA for injection, gene gun particles, liposomes including cationic liposomes, virosomes, receptor-mediated delivery vehicles, and biodegradable and non-biodegradable polymer matrixes.

Camptothecin drugs complexed in a reversible manner to oligonucleotides (for both water-soluble oligonucleotide-camptothecin drug complexes or oligonucleotide-camptothecin drug complexes contained in particles such as virus particles) can gain entry into cancer cells. Because the drugs are reversibly complexed with the oligonucleotides, the drugs can dissociate from the oligonucleotides and be able to exert their effect on the topoisomerase I target within the cancer cell. In the special case where covalent interactions between camptothecin drug and oligonucleotide put the drug in closer proximity to the macromolecule, such that the probability of lactone binding and stabilization is greater, cellular metabolism will be necessary to release the drug from the oligonucleotide.

The oligonucleotide-camptothecin drug complexes can be further incorporated into macromolecular assemblies for optimization of controlled drug release and delivery characteristics. The oligonucleotide-DNA complexes can consist of the following materials: biodegradable and non-biodegradable polymers, lipids, carbohydrates, proteins and biologically relevant molecules which facilitate the delivery, accumulation and processing of the oligonucleotides and drugs to target tissues within the human body. Each of the above oligonucleotide delivery vectors containing oligonucleotides can act to stabilize the lactone forms of camptothecin drugs. The oligonucleotide contained within the vectors can serve as a stabilizing matrix for the drug and the stabilization can be effective over a wide pH range; the vectors also provide a means for the controlled, targeted and stable delivery of camptothecin drug to target tissue. In addition to stabilizing camptothecin, the oligonucleotides carried in the vectors serve an additional role in exerting gene therapy or pharmacological effects in general which can be envisioned to augment the effects of camptothecins on the host target tissue and the patient receiving the therapy. The combination of stable camptothecin drug delivery and gene therapy can have potentially unique and desirable consequences on inhibiting the spread of cancer and other disease states in humans and animals.

BRIEF DESCRIPTION OF THE DRAWINGS

The accompanying drawing incorporated in and forming a part of the specification, illustrates several aspects of the present invention and together with the description serves to explain the principles of the invention. In the drawing.

DETAILED DESCRIPTION OF THE INVENTION

Figure 1:
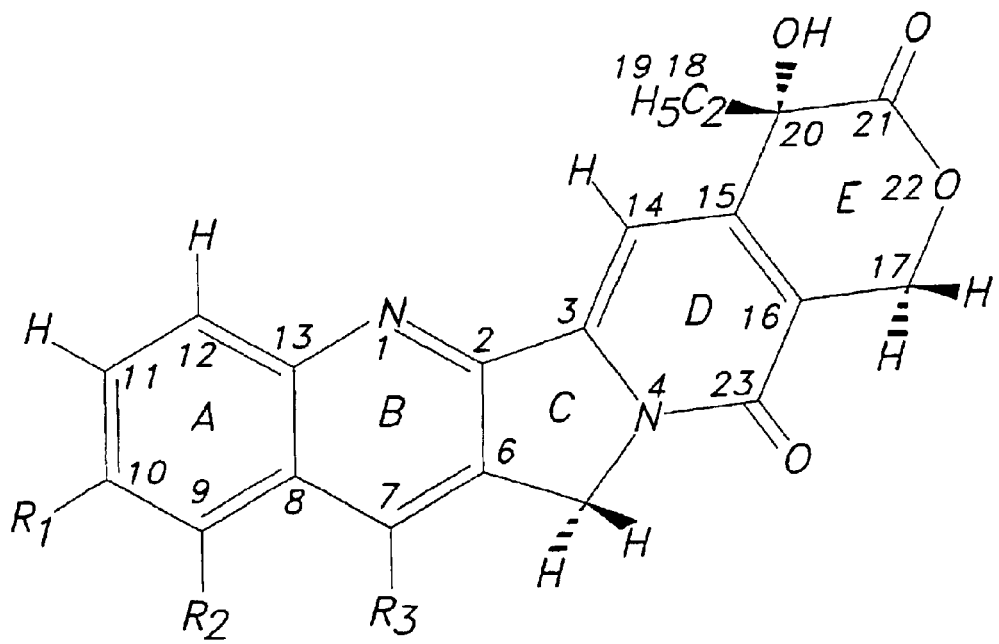
FIG. 1 is a summary of the structures of several clinically relevant camptothecins including camptothecin (CPT), CPT-11, SN-38, and topotecan (TPT). Also shown at the bottom of the figure are the D and E rings of the drugs, with the depiction showing the pH-dependent conversion between the lactone and carboxylate forms of the drug. At physiological pH the carboxylate form of the drug is by far the predominant form of the drug.
Figure 1:
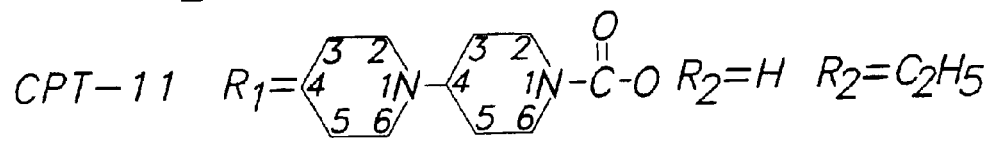
Figure 1:
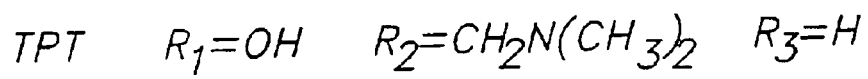
Figure 1:
Figure 1:
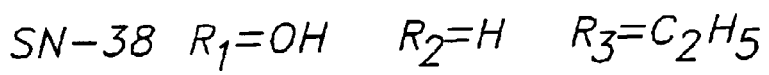
Figure 1:
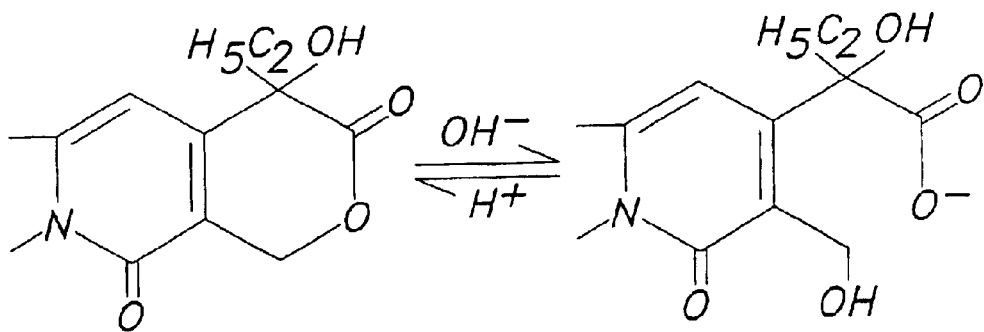

Camptothecin drugs are a family of agents which exhibit very high potencies against a wide and diverse range of tumor types and thus camptothecin drugs are useful anticancer agents. Likewise, oligonucleotides can be used as effective anticancer drugs. Cancer has been shown to be a somatic genetic disorder with gene dysfunctions that accumulate as the tumor progresses from premalignant lesions to malignant transformations. Oligonucleotides containing genetic information can be transferred to specific target cells in the body to prevent and limit the spread of cancer cells.

This technology, widely referred to as gene therapy, requires the oligonucleotide or genes and their regulatory elements as well as vectors such as cationic liposomes or adenoviruses to introduce the genes into the patients target cells for therapeutic activity.

There are several reasons why combination camptothecin drug-gene therapy dosage forms may prove to be promising technologies for cancer treatment. Hematologic malignancies and solid tumors contain cells that are highly responsive to the presence of camptothecin drugs. As a result of the stable delivery of the bioactive lactone forms of camptothecin drugs facilitated by the presence of the oligonucleotide, tumor size can be reduced and the spread or metastasis of the tumor can be halted. A number of genetic mechanisms of cancer development and progression have been discovered, leading to genetic, oligonucleotide-based therapies for treatment. The combination of the two therapeutic substances, active lactone camptothecin drugs and oligonucleotides, provide significant advantages at inhibiting the progression of solid tumors and hematologic malignancies. Whereas the camptothecin drugs can destroy cancer cells by inhibiting the proper function of topoisomerase I enzyme, oligonucleotide-based gene therapy can potentially augment the camptothecin therapy by modulating cytokine/immunotherapy, drug sensitivity genes, tumor suppressor genes, and drug resistance genes, and genes involved in angiogenesis. While the presence of the oligonucleotide serves as a stabilizing matrix where noncovalent binding interactions stabilize the camptothecin drug in the active lactone form, the oligonucleotide also can have a therapeutic effect that can enhance, prolong, and have a desirable combined effect with the camptothecin drug. Other objects and advantages of the present invention involving oligonucleotide-camptothecin drug formulations will become apparent as to the description thereof proceeds.

Typically, viral or non-viral vectors are used to deliver the gene therapy oligonucleotides to target cancer cells. The viral vectors include the following: retroviruses, adenoviruses, adeno-associated viruses, Herpes viruses, Vaccinia viruses, and polioviruses. The non-viral vectors include transfection, naked DNA injection, gene gun, direct injection, cationic liposomes, virosomes, and receptor-mediated delivery vehicles. Each of the above gene therapy vectors contain oligonucleotides which can act to stabilize the camptothecin drug. The vectors thus serve as a means of delivering stable camptothecin drug to target tissue. The combination of stable camptothecin drug and gene therapy has potentially unique and desirable consequences on 110 inhibiting the spread of cancer in humans and animals.

Of the non-viral and viral vectors, liposomes and cationic lipids have the advantage of being safe, readily reproducible and easy to manufacture. Liposomes containing oligonucleotides can more effectively stabilize the camptothecin drug in the antitumor-active lactone form. Oligonucleotide-containing liposomes provide a convenient mode of delivery for combination therapy comprising chemotherapy/gene therapy.

In satisfaction of the foregoing objects and advantages, there is provided by this invention oligonucleotide compositions for delivery of camptothecin drugs. Those compositions comprise at least one camptothecin drug in complex formation with an oligonucleotide including DNA and RNA so that the camptothecin drug contains a stabilized lactone ring. Additionally, the compositions include components which comprise viral and non-viral vectors such as proteins, lipids, and carbohydrates.

Oligonucleotides

The oligonucleotide which stabilizes the camptothecin drug of interest can be any of the following general types: B-Form DNA, A-Form DNA, C-Form DNA, D-Form DNA, T-Form DNA, Z-DNA, double-stranded DNA: single-stranded DNA, negatively-supercoiled DNA, nicked DNA, positively-supercoiled DNA, plasmid DNA, circular or cDNA, interwound or toroidal coiled DNA, catenaned or knotted DNA, helical DNA, hairpin DNA, interstrand crosslinked DNA, DNA in Cruciform structures, intermolecular triplex DNA, intramolecular triplex DNA, four stranded DNA, Anisomorphic DNA, genomic DNA, nucleosomal DNA, chromosomal DNA, antisense oligonucleotides, ribozymes, triplex-forming oligonucleotides, nuclease-resistant DNA therapeutics, self-assembled oligonucleotides as antisense agents, circular oligonucleotides, peptide nucleic acids, stabilized RNA analogs for antisense and ribozyme applications, phosphodiester and chimeric oligonucleotides, protein-antisense oligonucleotide conjugates, antibody-antisense oligonucleotide conjugates, messenger RNA, Hoogsteen DNA, phosphorothioate oligonucleotides, phosphodiester oligonucleotides, methylphosphonate oligonucleotides, alphavirus DNA, mitochondrial DNA, DNA plasmid shuttle vectors, hammerhead ribozymes, hairpin ribozymes, oligonucleotide cleaving ribozymes, antisense RNA, viral vector DNA, pararetroviral and retroviral DNA, N-linked oligosaccaride DNA, self-splicing group 1 intron ribozymes, self-splicing group II intron ribozymes, ribonuclease P(RNAase P) ribozyme, hepatitis delta virus ribozymes, hairpin ribozymes, anti-HIV ribozymes, raf oliogdeoxyribonucleotide, and catalytic DNA.

The nucleic acids which are useful in the present invention are those that form drug-oligonucleotide complexes in solution as well as those that form drug-oligonucleotide complexes in non-viral or viral delivery vehicles. The nucleic acids are typically nucleotide polymers having from 10 to 500,000 nucleotide residues. Typically, the nucleic acids of interest are to be administered to a subject for the purpose of repairing or enhancing or diminishing the expression of a cellular protein. In addition, the nucleic acid 110 may carry a label (e.g. radioactive label, fluorescent label or calorimetric label), these labels serving the purpose of providing clinical diagnosis relating to the presence or absence of complementary nucleic acids. Accordingly, the nucleic acids or nucleotide polymers can be nucleic acid polymers including genomic DNA, cDNA, mRNA or oligonucleotides containing nucleic acid analogs. An example of these molecules is provided by the antisense derivatives as summarized in a recent review (Stein et al., Science 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences within the oligonucleotide.

The nucleotide polymers can be single-stranded DNA or RNA, or double-stranded DNA or DNA-RNA hybrid molecules. Examples of double-stranded DNA include structural genes or genes including control and termination regions, or self-replicating systems such as plasmid DNA.

Examples of single-stranded nucleic acids include antisense oligonucleotides (complementary to DNA and RNA), ribozymes and triplex-forming oligonucleotides. Approaches to enhancing the chemical stabilities of oligonucleotides have been developed. For enhance stabilities the single-stranded nucleic acids will preferably have some or all of the nucleotide linkages substituted with stable, nonphosphodiester linkages. Such substitutions include phosphorothioate, phosphorodithioate, phosphoroselenate, or O-alkyl phosphotriester linkages.

The nucleic acids used in the present invention may also involve nucleic acids in which modifications have been made in one or more sugar moieties and/or in one or more of the pyrimidine or purine bases. Sugar modifications can include replacement of one or more hydroxyl groups with halogens, alkyl groups, azido groups or functionalized as ethers or esters, and amines. Additionally, complete replacement of the sugar moiety may be carried out resulting in sterically and electronically similar structures, including aza-sugars and carbocyclic sugar analogs. Examples of modifications in the purine or pyrimidine base moiety include, for example, alkylated purines and pyrimidines, acylated purines or pyrimidines, or other heterocyclic substitutes known to those of skill in the art.

Our innovation can also use multiple genetic sequences. In this manner, the sequences for different proteins may be located on one strand or plasmid. Promoter, enhancer, stress or chemically-regulated promoters, antibiotic-sensitive or nutrient-sensitive regions, as well as therapeutic protein encoding sequences, may be included into the oligonucleotide of interest as required. Non-encoding sequences can also be included in the oligonucleotide of interest.

The nucleic acids employed in the present invention can be isolated from natural sources, or obtained from sources such as the ATCC or GenBank collections of compounds, or the nucleic acids can be prepared either by manual or automated synthetic methods. Synthetic nucleic acids can be prepared by a variety of solution or solid-phase reaction schemes. In general, solid-phase synthesis is the preferred method. Detailed descriptions of the procedures for solid phase synthetic methodologies of nucleic acids by phosphite-triester, phosphotriester, and H-phosphonate chemistries are now widely available through out the literature. Examples of solid-phase synthetic methods of nucleic acids can be found in the following references: Itakura, U.S. Pat. No. 4,401,796; Caruthers, et al., U.S. Pat. Nos. 4,458,066 and 4,500,707; Beaucage, et al., *Tetrahedron Lett.,* 22:1859–1862 (1981); Matteucci, et al., *J. Am. Chem. Soc.,* 103:3185–3191 (1981); Caruthers, et al., *Genetic Engineering,* 4:1–17 (1982); Jones, chapter 2, Atkinson, et al., chapter 3, and Sproat, et al., chapter 4, in *Oligonucleotide Synthesis. A Practical Approach,* Gait (ed.), IRL Press, Washington D.C. (1984); Froehler, et al., *Tetrahedron Lett.,* 27:469–472 (1986); Froehler, et al., *Nucleic Acids Res.,* 14:5399–5407 (1986); Sinha et al. *Tetrahedron Lett.,* 24:5843–5846 (1983); and Sinha, et al., *Nucl. Acids Res.,* 12:4539–4557 (1984).

Nucleic acids which when introduced into animals or humans provide physiological effects are included in this invention. In this manner nucleic acids can be selected for specific therapeutic outcomes that complement or enhance the therapeutic benefit which is achieved by co-administration of the oligonucleotide-stabilized camptothecin.

An example of how nucleic acid-camptothecin drug co-administration can be therapeutic is given by the administration of a camptothecin drug with an anti-angiogenic oligonucleotide. Upon reaching the tumor site the camptothecin drug can exert its cytotoxic effect and thereby reduce the tumor size by destroying cancer cells. A major cause of cancer is often the regrowth of the tumor following the first round of chemotherapy. The regrowth of a tumor following a course of chemotherapy has been frequently attributed to vascularization of the tumor site, a process which brings nutrients to the tumor which in turn facilitates regrowth of the tumor. Thus it may be considered therapeutically desirable to treat a patient with anti-angiogenic compounds following reduction of tumor size with camptothecin chemotherapy.

Genetic material of choice would be an oligonucleotide which slows or eliminates the angiogenic process. Such a therapeutic approach could involve the use of an oligonucleotide that reduces or prevents the expression of a key angiogenic protein. Or the oligonucleotide approach could include genes encoding anti-angiogenic polypeptides either absent or produced in diminished quantities in the cancer patient being treated. The nucleic acids could also reverse the expression of mutant, non-functional forms of anti-angiogenic proteins. Additionally it may be of interest to use oligonucleotides such as DNA encoding polypeptides for secretion from target cells so as to provide for a systemic effect by the protein encoded by the DNA. Specific DNA molecules of interest include those encoding hemoglobin, interleukin-1, interleukin-2, interleukin-3, interleukin-4, interleukin-4, interleukin-5, interleukin-6, interleukin-7, interleukin-8, interleukin-9, interleukin-10, interleukin-11, etc., GM-CSF, G-CSF, M-CSR, human growth factor, insulin, factor VIII, factor IX, tPA, a variety of nuclear binding proteins and DNA topology modifying enzymes such as topoisomerases I, topoisomerase II, topoisomerase III, LDL receptors, tumor necrosis factor, PDGF, EGF, NGF, EPO, $\beta$-globin and the like, as well as biologically active mutants of these proteins. The nucleic acid utilized may also be antisense DNA or RNA. These antisense molecules can bind to naturally-occurring DNA or RNA within the host and block the production of molecules which can counteract, overcome, or negate the pharmacological effects achieved by the administration of camptothecins administered in oligonucleotide-stabilized form.

Further to this concept of co-administration of cytotoxic camptothecins and anti-angiogenic oligonucleotides, prevention of blood vessel growth could be achieved by modulating the levels of the numerous types of growth factors and proteins involved in the angiogenesis process [Folkman, et al., *Science,* 235:442–447 (1987)]. These key angiogenic components include, for example, acidic and basic fibroblast growth factors (alpha-FGF and beta-FGF), vascular endothelial growth factor (VEGF), epidermal growth factor (EGF), transforming growth-factor $\alpha$- and $\beta$-(TGF-$\beta$ and TGF-$\beta$), platelet-derived endothelial cell growth factor (PD-ECGF), platelet-derived growth factor (PDGF) itself, tumor necrosis factor $\alpha$-(TNF-$\alpha$), hepatocyte growth factor (HGF) and insulin like growth factor [See, Klagsbrun, et al., *Annu. Rev. Physiol.,* 53:217–239 (1991) and Folkman, et al., *J. Biol. Chem.* 267:10931–10934 (1992)]. VEGF, or its alternate designation vascular permeability factor (VPF), has also been implicated in the angiogenesis process, and oligonucleotides co-administered with camptothecins may also be useful in modulating VEGF levels and optimizing the anticancer effects of the camptothecins. VEGF is a key angiogenic protein. Evidence that VEGF stimulates the angiogenesis in vivo had been developed in experiments performed on rat and rabbit cornea (Levy, et al., *Growth Factors,* 2:9–19 (1989) and Connolly, et al., *J. Clin Invest.,* 84:1470–1478 (1989)), the chorioallantoic membrane (Ferrara, et al., Biochem Biophys Res Commun., 161:851–855 (1989)), and the rabbit bone graft model. Connolly, et al., *J Clin Invest.,* 84:1470–1478 (1989). The nucleotide sequence of numerous peptides and proteins, including angiogenic proteins such as VEGF, are readily available through a number of computer data bases, for example, GenBank, EMBL and Swiss-Prot. Through gene therapy methods, the levels of proteins involved in the angiogenic process can be modulated and the activities of oligonucleotide-stabilized camptothecin drug delivery vehicles optimized for gains in therapeutic outcomes for the cancer patients.

Antisense RNA molecules can also potentially be used to optimize the therapeutic activities of the camptothecin drugs delivered to the body in a stable form by complexing with oligonucleotide. Antisense RNA molecules are known to be effective at regulating translation within the cell. Using known methods antisense RNA molecules can be produced from the corresponding gene sequences. The antisense molecules can be used as a therapeutic to regulate gene expression that optimizes camptothecin activity within the body. The antisense molecules are typically designed by studying the nucleotide sequence, and by reversing the orientation of the coding region with regard to the promoter. Accordingly, the antisense RNA is complementary to the corresponding mRNA. Reviews of antisense design can be found elsewhere [Green, et al., *Ann. Rev. Biochem.* 55:569–597 (1986)]. The antisense sequences can contain modified sugar phosphate backbones which is a widely used approach that allows for the increased stabilities of the antisense molecules following their introduction into humans or animals. The changes in the antisense RNA can also be used to make the antisense molecules less sensitive to RNase activity. Examples of these types of antisense modifications are described by Rossi, et al., *Pharmacol, Ther.* 50(2):245–354, (1991). Co-complexation of camptothecin drugs with multidrug resistance (MDR) and/or multidrug resistance-associate protein (MRP) antisense RNAs would result in the camptothecin drugs proving to be cytotoxic to the cancer cells and the ribozymes would prevent drug resistance from advancing at the tumor site. Methods for the preparation and use of MDR and MRP antisense RNAs to modulate drug resistance have been reported previously (Gao et al., Anticancer Res. (1998) 18:4 3073–6).

Viral Delivery Vectors

Viral or non-viral vectors can be used to deliver the oligonucleotide-camptothecin drug complexes to the target cells. The viral vectors can include the following: retroviruses, adenoviruses, adeno-associated viruses, Herpes viruses, Vaccinia viruses, and polioviruses.

Retroviruses contain RNA and DNA. The RNA genome consists of two 8500-nucleotide RNA molecules noncovalently bonded to one another. The virus is enclosed by a lipid bilayer. Hence the retrovirus can serve as vehicle for delivering of oligonucleotides to the body, but also as a vehicle where camptothecin drugs can be introduced, stored and delivered in a stable manner while being bound in the active lactone form to the oligonucleotides contained in the retrovirus. Addition of cationic lipids to retroviruses could augment the delivery of the drug and oligonucleotide content to cancer cells. In a similar manner, adenoviruses, SV40, Herpes viruses, Vaccinia viruses, Parvoviruses, Reoviruses, Influenza viruses, Vesicular stomatitis virus, Sindbis virus, poliomyelitis virus, human wart virus, adenovirus are all viruses that contain oligonucleotides that can serve the multiple roles of complexing, stabilizing, transporting, and delivering camptothecin drugs in humans and animals while also delivering oligonucleotides that are capable of inducing pharmacological effects that differ from the camptothecin drugs. The pharmacological effects of the oligonucleotides contained in the virus particles can augment, complement and provide synergism with the camptothecin drug therapy.

Non-Viral Delivery Vectors

The non-viral vectors include transfection, naked DNA injection, gene gun, direct injection, cationic liposomes, virosomes, and receptor-mediated delivery vehicles. Each of the above gene therapy vectors contain oligonucleotides which can act to stabilize the camptothecin drug of interest. The vectors thus serve as a means of delivering stable camptothecin drug to target tissue. The combination of stable camptothecin drug and gene therapy has potentially unique and desirable consequences on inhibiting the spread of cancer in humans and animals.

To simplify the manipulation and handling of the DNA, prior to introduction into animals and humans, the DNA is preferably inserted into a vector, e.g., a plasmid vector such as pUC118, pBR322, or other known plasmid vectors [Sambrook, et al., *Molecular Cloning: A Laboratory Manual*, Cold Spring Harbor Laboratory press, (1989)]. The plasmid vector may also include a selectable marker such as the β-lactamase gene for ampicillin resistance, provided that the marker polypeptide does not adversely effect the metabolism of the organism being treated. Additionally, if necessary, the DNA may be operably linked to a promoter/enhancer region capable of driving expression of the protein in the target cell of interest. An example of an appropriate promoter is the cytomegalovirus (CMV) promoter. Normally, an enhancer is not necessary when the CMV promoter is used. Other promoters may be used as well. Certain proteins can be expressed using their native promoter.

In certain situations, it may be desirable to use DNA that encodes two or more different proteins in order to optimize the therapeutic outcome. For example, anti-angiogenic oligonucleotides can be combined with other genes or their encoded gene products to enhance the activity of targeted cells to camptothecin-based therapies.

Liposomes and cationic liposomes have been widely used to deliver DNA and antisense oligonucleotides to target tissues. Here we claim as a vehicle for oligonucleotide-stabilized camptothecin drug delivery a liposome or micelles having at least one membrane comprised of surfactant, lipid or mixture thereof wherein the membrane defines a closed compartment for holding the camptothecin drug and oligonucleotide complex. In this compartment the lactone ring of the camptothecin drug is protected from hydrolysis and fully stabilized by contributions made by the presence of the oligonucleotide. The oligonucleotide utilized in the present invention is selected from a group consisting of DNA and RNA, as well as mixtures thereof. Any of the oligonucleotides mentioned elsewhere in this document could be included in the liposomal preparations.

The present invention provides novel, lipid-oligonucleotide-camptothecin drug particles. The liposomes may comprise synthetic phospholipids, phosphatidic acids, phosphatidylethanolamines, phosphatidylgylcerols, phosphatidylserines, polymerizable phospholipids, phospholipid such as egg phosphatidylcholine, hydrogenated soy phosphatidylcholine, distearoylphosphatidylcholine, dimyristoylphosphatidylcholine, distearoylphosphatidylcholine, or diarachidonoylphosphatidylcholine, and may additionally comprise cholesterol, for example, in about a 55:45 to 75:25 phospholipid:cholesterol mol ratio. The liposomes may additionally comprise alpha tocopherol. The liposomes can be about 30 nm to about 10 microns in size, preferably about 100 to about 300 nm in diameter. The technology can include large unilamellar vesicles or multilamellar liposomes, or complexes of varying shapes as well. They can contain about 0.05 to 200 mg/ml lipid, more preferably about 5 to about 110 mg/ml lipid. The entrapment of the oligonucleotide-camptothecin drug complex in the liposomes is from about 50% to about 100%, preferably about 90% to about 100%, more preferably about 98 to about 100%. These liposome may be large unilamellar vesicles or multilamellar particles. The liposomes may be homogeneous or unimodal with regard to size distribution.

Pharmaceutical preparations containing the oligonucleotide-camptothecin drug complex entrapped in the liposomes and pharmaceutically acceptable carriers or diluents are another embodiment of the present invention. The liposome compositions of the invention may be used to treat cancer. In related applications, the liposomal formulations can be used prophylactically to prevent the onset or recurrence of a cancer. The composition of the present invention is, for example, provided also as a three-component system. The three component system comprises empty liposomes in a solution ranging from about pH 3.0 to pH 8.0, and the oligonucleotide-camptothecin drug complex. The solution can be acetic acid buffer, oxalic acid buffer, or succinic acid buffer, preferably aqueous citric acid buffer. The basic solution is preferably sodium carbonate. The complex to lipid weight ratio is greater than about 0.1:1 to about 3:1.

Polymerizable phospholipids that can be used in this include polymerizable double-bond containing monomeric phospholipids. The polymerizable phospholipids to be used in this invention must contain at least one polymerizable moiety, but may include several polymerizable groups as well. Polymerizable groups located in the phospholipids can contain, but need not be limited to, the following: diacetylenes, olefins, acetylenes, and thiols as well. The polymerization process can be initiated by free radical initiators such as azo-bis-isobutyronitrile (AIBN) or other initiators as well including azo-bis-amidinopropane dihydrochloride). Other methods of initiating polymerization include using ultraviolet light or gamma irradiation.

The liposome compositions may be prepared by remote loading techniques, which rely on a pH or chemical gradient across the liposome bilayer to load camptothecin drugs into liposomes containing oligonucleotide-camptothecin drug complexes isolated or in contact with the lipid matrix. A first step would involve forming the oligonucleotide-containing liposomes in a aqueous medium, preferably a buffer. The solution outside the liposomes is then exchanged or modified by acidifying or alkalinizing the medium, thereby establishing a pH or chemical gradient. Care is taken not to subject the liposomal particles to osmotic stress through these manipulations. The resulting liposomes are then admixed with the camptothecin drugs, which can be prepared by contacting the liposomal-oligonucleotide solution and camptothecin drug solution, or liposome compositions may be prepared from oligonucleotide-camptothecin drug complex and lipids in either detergent-based or organic solvent-based systems, followed by removal of the detergent or organic solvent, leading to particle formation.

The liposomes of the invention may be dehydrated, either prior to or following the establishment of the remote loading techniques, which rely on a pH (*Biochim. Biophys. Acta,* 857, 123, 1986) or chemical gradient (*J. Natl. Cancer Inst.,* 81, 1484, 1989). Thus, the present invention provides methods of preparing oligonucleotide-camptothecin drug particles which are useful for the therapeutic delivery of oligonucleotide and camptothecin drugs for combination therapy. Within a liposomal formulation both the oligonucleotides and oligonucleotide-camptothecin drug complexes become protected from degradation. The liposomes thus formed are suitable for pharmaceutically acceptable liposomal formulations which allow direct parenteral administration of lactone stable oligonucleotide-camptothecin drug complexes to human patients with cancer. Pharmaceutically acceptable liposomal formulations which allow the direct oral administration of oligonucleotide-camptothecin drug complexes to human patients with cancer and other disease states are also claimed in the current invention.

Briefly, one method of forming lipid-oligonucleotide-camptothecin drug particles involves contacting an oligonucleotide solution and a camptothecin drug solution to form a oligonucleotide-camptothecin drug complex solution then contacting that oligonucleotide-camptothecin drug complex solution with a solution of lipids and a detergent to form a oligonucleotide-camptothecin drug-lipid mixture, followed by removal of the detergent or organic solvent. Another method involves first forming the liposomes containing oligonucleotide in aqueous medium, preferably a buffer, then acidifying or alkalinizing the medium, thereby establishing a pH or chemical gradient. The resulting liposomes are then admixed with a solution containing lipophilic camptothecin drugs that can partition into the pre-formed particles or ionizable, amine-containing camptothecin drugs that can accumulate in the liposomal particle in response to the ion gradient across the liposomal membrane. Another method of forming lipid-nucleic add particles involves the following: 1) contacting an amount of cationic lipids with oligonucleotide-camptothecin drug complex in a solution; 2) the solution comprising of from about 15–35% water and about 65–85% organic solvent and the amount of cationic lipids being sufficient to produce a +/− charge ratio of from about 0.1 to about 200.

To provide a hydrophobic, charge-neutralized lipid-oligonucleotide-camptothecin drug complex, the following procedure can be used: contacting the hydrophobic, charge-neutralized lipid-oligonucleotide-camptothecin drug complex in solution with non-cationic lipids, to provide a lipid-oligonucleotide-camptothecin drug complex mixture; and removing the organic solvents from the lipid-oligonucleotide-camptothecin drug complex mixture to provide lipid-oligonucleotide-camptothecin drug complex particles in which the nucleic acids are protected from degradation and the oligonucleotide-drug complexes aid in stabilizing the drug.

The following lipids can be used in the formation of camptothecin-lipid-oligonucleotide complexes: DC-Chol, 3β-(N—(N',N'-dimethylaminoethane)carbamoyl) cholesterol (see, Gao, et al., *Biochem. Biophys. Res. Comm.* 179:280–285 (1991)); DDAB, N,N-distearyl-N,N-dimethylammonium bromide; DMRIE, N-(1,2-dimyristyloxyprop-3-yl)-N,N-dimethyl-N-hydroxyethyl ammonium bromide; DODAC, N,N-dioleyl-N,N-dimethylammonium chloride; DOGS, diheptadecylamidoglycyl spermidine; DOPE, 1,2-sn-dioleoylphoshatidylethanolamine; DOSPA, N-(1-(2,3-dioleyloxy)propyl)-N-(2-(sperminecarboxamido)ethyl)-N, N-dimethylammonium trifluoroacetate; DOTAP, N-(1-(2,3-dioleoyloxy)propyl)-N,N,N-trimethylammonium chloride; DOTMA, N-(1-(2,3-dioleyloxy)propyl)-N,N,N-trimethylammonium chloride; ESM, egg sphingomyelin. The term "lipid" refers to any suitable material resulting in macromolecular assembly such as bilayer, monolayer, lipid-DNA complex, such that a hydrophobic portion of the lipid material orients toward the monolayer, bilayer, or DNA-lipid complex while a hydrophilic portion orients toward the aqueous phase. Amphipathic lipids are necessary for the formation of the primary lipid vesicle structural element. Hydrophilic characteristics of these agents derive from the presence of phosphate, carboxylic, sulfato, amino, sulfhydryl, nitro, and other similar functionalities. Hydrophobicity in the lipids can be conferred by the inclusion of groups that include, but are not limited to, long chain saturated and unsaturated aliphatic hydrocarbon groups, and groups substituted with one or more aromatic, cycloaliphatic or heterocyclic groups. The term "neutral lipid" refers to any of a number of lipid species which exist either as uncharged or neutral zwitterionic species at physiological pH. The group of neutral lipids are comprised of amphiphiles such as diacylphosphatidylcholine, diacylphosphatidylethanolamine, ceramide, sphingomyelin, cephalin, and cerebrosides.

The term "non-cationic lipid" refers to any neutral lipid as described above as well as anionic lipids. Examples of anionic lipids include the following: cardiolipin, diacylphosphatidylserine and diacylphosphatidic acid. The term "cationic lipid" refers to any of a number of lipid species which carry a net positive charge at physiological pH. Such lipids include, but are not limited to, DODAC, DOTMA, DDAB, DOTAP, DC-Chol and DMRIE. Additionally, a number of commercial preparations of cationic lipids are available which can be used in the present invention. These include, for example, LIPOFECTIN (commercially available cationic liposomes comprising DOTMA and DOPE, from GIBCO/BRL, Grand Island, N.Y., USA); LIPOFECTAMINE (commercially available cationic liposomes comprising DOSPA and DOPE, from GIBCO/BRL); and TRANSFECTAM (commercially available cationic lipids comprising DOGS in ethanol from Promega Corp., Madison, Wis., USA). This invention can also employ polymerizable phospholipids where polymerizable moieties are included in the headgroup region of the phospholipid and/or in the acyl chain region of the phospholipid.

The term "transfection" as used herein, refers to the introduction of polyanionic materials, particularly nucleic acids, into cells. The term "lipofection" refers to the delivery of such materials using liposome complexes to cells. The polyanionic materials can be in the form of RNA or DNA incorporated into expression vectors. The involvement of expression vectors facilitates gene expression following entry into the cell. Polyanionic material can be used in the present invention and is meant to include oligonucleotides having coding sequences for structural proteins, receptors and hormones, as well as transcriptional and translational regulatory elements (i.e., promoters, enhancers, terminators and signal sequences) and vector sequences. Incorporation of particular nucleic acids into expression vectors are known methods to those of skill in the art, but are described in detail elsewhere, for example: Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference. The terms "expression vectors", "cloning vectors", or "vectors" are used to refer to plasmids or other nucleic acid-derived materials that are able to replicate in a chosen host cell. Expression vectors may replicate autonomously, or they may replicate by being inserted into the genome of the host cell, and these methods are well known to those experienced in the art. Vectors that replicate autonomously will have an origin of replication or autonomous replicating sequence (ARS) that is functional in the target cells and tissues of interest. Often, it is desirable for a vector to be usable in a variety of cell types, e.g., particularly in mammalian cells.

The term "hydrophobic" as applied to DNA and DNA complexes implies complexes which are substantially more soluble in organic solvents than in aqueous solutions. More particularly, hydrophobic DNA and DNA complexes are aggregates which are at least 40% soluble in organic solvents such as chloroform/methanol mixtures, and preferably more than 80% soluble, more preferably more than 90% soluble in such organic solvents.

The current invention can employ formulations with lipids exhibiting different transition temperatures and vesicles sizes. Multilamellar vesicles (MLVs), large unilamellar vesicles (LUVs), and small unilamellar vesicles (SUVs) at concentrations ranging from 0.5 mg/ml to 200 mg/ml can be prepared through a hydration process. Lyophilized formulations of liposomal oligonucleotide-camptothecin drug-lipid can be employed in this invention as well. Vials containing the oligonucleotide-camptothecin drug-lipid complexes will be obtained by freeze-drying solutions containing these ingredients in mixtures of t-butanol and water (drug:lipid ratios in the range of 1:10 to 1:200 would be desirable). In light of the high levels of lipophilicity that we have observed in some of the new analogues ($K_{DMPC}$=8,000 $M^{-1}$ versus $K_{DMPC}$=1$M^{-1}$ for other camptothecins), the camptothecin drugs will have the ability to interact with the liposomal particles in a number of different ways, dependent upon the individual drug structure. Following lyophilization, the liposomes for i.v. administration will be reconstituted by adding PBS to the vial containing lyophilized particles and mixing for several minutes.

The following lipid combinations and particle types are suitable for use in this invention: Egg-PC/Cholesterol (SUV, LUV and MLV); DPPC/DPPG/cholesterol (SUV, LUV and MLV ratio 8:5:4 or thereabout); DPPC/DPPG (SUV, LUV and MLV; lipid ration of 5:2 or thereabout); DMPC:DMPG (SUV, LUV, MLV; lipid ratio of 14:1 or thereabout); Egg-PC/Egg PG/Cholesterol (SUV, LUV and MLV; lipid ratios of 4:2:1 or thereabout); DSPC/DSPG/gm 1/Sphingomyelin Cholesterol (SUV and MLV; ratio 8:5:4:1:1 or thereabout); DPPC/DPPA (SUV and MLV; lipid ratio of 5:6:2 or thereabout); DMPC:DMPA (SUV, LUV, MLV; lipid ratio of 14:1 or thereabout); HPC/PEG (MLV and SUV; lipid ratio of 5:1 or thereabout); Egg-PG/Cholesterol (SUV, LUV and MLV; lipid ratio 2:1 or thereabout); DPPG/cholesterol (SUV, LUV and MLV ratio 8:4 or thereabout); DPPG/DPPA (SUV, LUV and MLV; lipid ration of 5:1 or thereabout); DMPC:DSPC (SUV, LUV, MLV; lipid ratio of 14:1 or thereabout); Egg-PC/Egg PG/Cholesterol/DPPA (SUV, LUV and MLV; lipid ratios of 4:2:1:1 or thereabout); DMPC/DSPC/Sphingomyelin/Cholesterol (SUV, LUV and MLV; ratio 8:5:4::1 or thereabout); DPPC/egg PE (SUV, LUV and MLV; lipid ratio of 5:2 or thereabout); DMPC:D-MPA:DSPC (SUV, LUV, MLV; lipid ratio of 14:1:3); HPC/cholesterol (MLV, LUV and SUV; lipid ratio of 5:1 or thereabout).

The drug/lipid mixtures can be prepared in a suitable solvent such as chloroform and then dried under a stream of nitrogen gas. Lipid films resulting from this process can then be dried under high vacuum for 1–24 hrs. to properly assure the removal of trace chloroform. Dried lipid/drug films can be hydrated in solutions of varying pH values. In some cases liposome preparations can be frozen/thawed several times prior to extrusion through stacked polycarbonate filters of specific pore size to reduce the particle size. In some cases MLVs will be sonicated to prepare small MLVs and SUVs. During formulations samples can be heated to approximately 1 to 10° C. above the thermotropic phase transition temperatures of the phospholipids contained in the preparations prior to the extrusion or sonication process. Particle sizing of the preparations can be performed using commercially available particle sizers such as instruments made by Malvern or Coulter.

Cationic Amphiphiles and Polyamines

The cationic amphiphiles are often effective at transporting biologically-active therapeutics into cells. Additionally, targeting of organs for gene therapy by intravenous administration of therapeutic compositions can be achieved using such systems (as described in U.S. Pat. No. 5,719,131). Lipophilic groups of amphiphiles can be derivatives of steroids, functionalized amines, or derived from alkyl or acyl groups; and the cationic groups can by amines of modified amines, or polyalkylamines, which may be protonated at physiological pH. The therapeutic formulations are prepared by contacting a dispersion of cationic amphiphiles with the biologically-active molecules: in the present invention described herein it is camptothecin drugs in combination with DNA. Oligonucleotide-camptothecin drug complexes can be delivered to cells and this process can be facilitated using cationic amphiphiles. Representative uses of the therapeutic compositions containing lipid, oligonucleotides and cationic amphiphiles are as follows: gene therapy, anticancer therapy, diseases involving inflammation and infectious diseases. The oligonucleotide therapeutics are provided in the form of a plasmid in combination with camptothecin drugs, and cationic amphiphiles capable of interacting with both the lipid, oligonucleotide and oligonucleotide-camptothecin drug complex.

Certain amphiphiles and neutral molecules as well can covalently associate with macromolecules. An important example of these types of agents are photosensitizers. These agents are exemplified by prophyrin-based photosensitizers, including prophyrins, chlorins, bacteriochlorins, polypyrrolic macrocycles phthalocyanines. The photosensitizers, especially prophyrins can conjugate biomolecules, including biological active molecules such as steroids, lipids, peptides, nucleosides, nucleotides, antibody conjugates, steroid conjugates, sugar conjugates, and mono and polynucleotide conjugates. Peptides along with other compounds such as membrane transport molecules and DNA ligands can also be conjugated. The photosensitizers can be activated by light in order to covalently bind the agent to DNA. The camptothecins can be photoactivated and complexed to DNA as well (Leteurtre et al., 1993). This invention claims oligonucleotide-camptothecin complexes and oligonucleotide-camptothecin drug in combination with other drugs where the agents have been covalently attached using light. Such covalently modified aggregates may exhibit improvements in terms of stabilizing and delivering the active agents to the tumor. Such covalently attached molecules useful for the desired purposes undergo disassembly upon reaching the tumor site thereby releasing active agent.

Polyamines can be used as carriers for oligonucleotide-camptothecin drug complexes. Polyamines are ubiquitous cell components, and these agents are essential for normal growth. Polyamine analogues, notably those with ethyl or benzyl groups on the terminal nitrogen atoms, have potent antiproliferative activity and are promising agents for the treatment of cancer. The association of cad onic polyamines with negatively-charged oligonucleotides induces significant structural changes in the macromolecules in cell-free systems. Spermine and spermidine can cause DNA to condense and aggregate and induce transition as in B-to-Z in certain DNA sequences. Because it is the binding of camptothecin lactone forms to DNA that result in stabilization of the active forms of the drug, oligonucleotide-camptothecin drug-polyamines and oligonucleotide-camptothecin drug-polyamine-lipid complexes should exhibit favorable influences on the drugs by acting to conserve the active lactone forms.

Cyclodextrins

Cyclodextrins can be used as cellular delivery systems for oligonucleotide-camptothecin-drug complexes. Oligonucleotides can bind noncovalently with substituted and non-substituted beta gamma cyclodextrin and derivatives. The uptake of oligonucleotides into cells can be modulated with cyclodextrin. The pharmaceutical formulation of oligonucleotide-camptothecin drug complex with cyclodextrin and oligonucleotide-camptothecin-lipid complex can render a physiologically acceptable carrier. The inclusion of cyclodextrins in camptothecin-lipid complexes can impact on biological activities by increasing the cellular uptake and accumulation of both the active lactone form of camptothecin drug and of the exogenous oligonucleotide included in the formulation. The formulations can be of potential utility in diseases such as cancer, infectious diseases such as in the case of viral infections, and inflammation. Formulation of oligonucleotide-camptothecin drug complexes and camptothecin-lipid-oligonucleotide complexes with cyclodextrins may be useful in increasing the solubility and stability of an oligonucleotide-camptothecin drug complex in vitro and in vivo.

Camptothecin Drugs

Preferably, the camptothecin drugs utilized in this invention are any of the known camptothecin drugs found in the prior art to have the necessary liposomal loading, low toxicity and high antitumor activity for the intended purpose. Examples of the camptothecin drugs that may be utilized include:

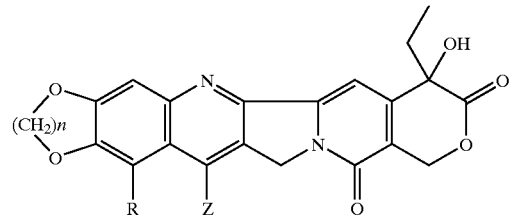

A) Wherein R is $NO_2$, $NH_2$, $N_3$ hydrogen, trimethylsilylmethylaminomethyl, halogen (F, Cl, Br, I)>COOH, OH, O—$C_{1-3}$ alkyl, SH, S—$C_{1-3}$ alkyl CN, $CH_2$ $NH_2$, NH—$C_{1-3}$ alkyl $CH_2$—NH—$C_{1-3}$ alkyl, $N(C_{1-3}$ alkyl$)_2$, $OCH_2CH_2N(CH_2CH_2OH)_2$, $NHCH_2CH_2N(CH_2CH_2OH)$, and $SCH_2CH_2N(CH_2CH_2OH)_2$, $OCH_2CH_2CH_2N(CH_2CH_2OH)_2$, $NHCH_2CH_2CH_2N(CH_2CH_2OH)_2$ and $SCH_2CH_2CH_2N(CH_2CH_2OH)_2$, $OCH_2CH_2N(CH_2CH_2CH_2OH)_2$, $NHCH_2CH_2N(CH_2CH_2CH_2OH)_2$ and $SCH_2CH_2N(CH_2CH_2CH_2OH)_2$, $OCH_2CH_2CH_2N(CH_2CH_2CH_2OH)_2$, $NHCH_2CH_2CH_2N(CH_2CH_2CH_2OH)_2$ and $SCH_2CH_2CH_2N(CH_2CH_2CH_2OH)$, $OCH_2CH_2N(C_{1-3}$ alkyl$)_2$, $NHCH_2CH_2N(C_{1-3}$ alkyl$)_2$ and $SCH_2CH_2N(C_{1-3}$ alkyl$)_2$, $OCH_2CH_2CH_2N(C_{1-3}$ alkyl$)_2$, $NHCH_2CH_2CH_2N(C_{1-3}$ alkyl$)_2$- and $SCH_2CH_2CH_2N(C_{1-3}$alkyl$)_2$, CHO or $C_{1-3}$ alkyl and Z is H, $C_{1-8}$ alkyl, trimethylsilyl, tertbutyldimethylsilyl, trimethylsilylmethyl, trimethylsilymethylaminomethyl t-butyldimethylsilylethyl, trimethylsilylethyl,

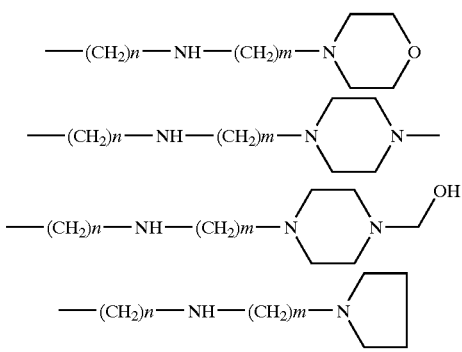

n=1–8; m=0–6 or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{2-6}$ alkenyl, hydroxy-$C_{1-6}$ alkyl $C_{1-6}$ alkoxy $C_{1-6}$ alkyl 5,6,7-membered heterocyclic rings contains one or more O, N, S (b)$R^1$ is hydrogen, $C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-$C_{1-6}$alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen nitro amino, $C_{1-6}$ alkylamino, perhalo-$C_{1-6}$ alkyl, hydro-$C_{1-6}$ alkyl, $C_{1-6}$ alkoxy, $C_{1-6}$ alkoxy-$C_{1-6}$alkyl and —$COR^5$ where $R^5$ is hydrogen, $C_{1-6}$ alkyl, perhalo-$C_{1-6}$ alkyl, $C_{1-6}$ alkoxy, aryl and aryl substituted with one or more $C_{1-6}$alkyl, perhalo-$C_{1-6}$ alkyl, hydroxy-$C_{1-6}$alkyl, or $C_{1-6}$ alkoxy-$C_{1-4}$ alkyl groups. In the structure shown above, n is an integer of 1 or 2. Preferred aryl groups are phenyl and naphthyl;

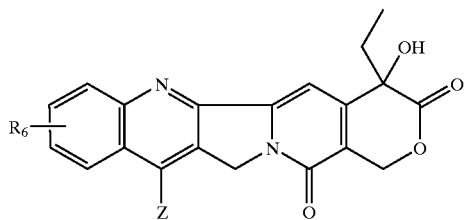

B) wherein $R^6$ is hydrogen, cyano, formyl, hydroxy, $C_{1-8}$ alkoxy, nitro, amino, halogen (I Br, Cl, F), $C_{1-8}$ alkyl, trifluoromethyl, trimethylsilylmethylamino, aminomethyl, azido, amido, hydrazino,

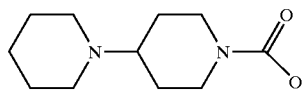

—$OC(O)R^7$ or $OC(O)$—$NR^7R^8$, where $R^7$ and $R^8$ are, independently hydrogen or $C_{1-8}$ alkyl; and Z is H, $C_{1-8}$ alkyl, trimethylsilyl, tertbutyldimethylsilyl, trimethylsilylmethyl, trimethylsilylmethylaminomethyl, t-butyldimethylsilylethyl, trimethylsilylethyl,

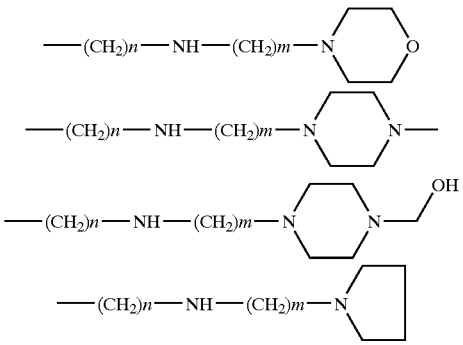

n=1–8; m=0–6 or $CH_2NR^1R^2$ where (a) $R^1$ and $R^2$ are, independently, hydrogen, $C_{1-6}$ alkyl, $C_{3-7}$ cycloalkyl, $C_{3-7}$ cycloalkyl-$C_{2-6}$ alkenyl, hydroxy-$C_{1-6}$alkoxy, $C_{1-6}$ alkoxy $C_{1-6}$-alkyl, 5,6,7-membered heterocyclic rings contains one or more O, N, S (b)$R^1$ is hydrogen, $C_{1-6}$ alkyl, $C_{3-7}$ cycloalkyl, $C_{3-7}$cycloalkyl-$C_{1-6}$ alkyl, $C_{2-6}$ alkenyl, hydroxy-$C_{1-6}$ alkyl or $C_{1-6}$ alkoxy-$C_{1-6}$ alkyl and $R^2$ is —$COR^3$ where $R^3$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl, $C_{2-6}$ alkenyl, hydroxy-$C_{1-6}$ alkyl, $C_{1-6}$ alkoxy, $C_{1-6}$ alkoxy-C, alkyl, or (c) $R^1$ and $R^2$ taken together with the nitrogen atom to which they are attached form a saturated 3–7 membered heterocyclic ring which may contain a O, S or $NR^4$ group, where $R^4$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$ alkyl, hydroxy-$C_{1-6}$ alkyl, $C_{1-6}$ alkoxy, $C_{1-6}$ alkoxy-$C_{1-6}$ alkyl and —$COR^5$ where $R^1$ is hydrogen, $C_{1-6}$ alkyl, perhalo-$C_{1-6}$ alkyl, $C_{1-6}$ alkoxy, aryl, and aryl substituted with one or more $C_{1-6}$ alkyl, perhalo-$C_{1-6}$ alkyl, hydroxy-$C_{1-6}$alkyl, or $C_{1-6}$ alkoxy-$C_{1-6}$ alkyl groups. In the structure shown above, n is an integer of 1 or 2. Preferred aryl groups are phenyl and naphthyl;

C. Additional camptothecin compounds of the present invention have the hydroxyl group at the 20-position esterified with:—Aromatic and aliphatic carboxylic acids, aliphatic carboxylic acid with the formula —$O(CO)$—$(CH_2)_m$—$CH_3$, where m=1–20, and polyethers; O-PEG-OH (MW=350–5000), O-PEG-OMe (MW=350–5000), -alpha-carboxyl group of a naturally occurring amino acid to form a group of the formula —$OC(O)$—$CH2)_m$—$NR^{10}R^{11}$, where m=1–6 or —$OC(O)CHR^9NR^{10}R^{11}$, where $R^9$ is the side chain of one of the naturally occurring α-amino acids, $R^{10}$ and $R^{11}$ are, independently, hydrogen or $C_{1-8}$, alkyl. Suitable side chains $R^9$ are the side chains of the amino acids glycine, alanine, valine, leucine, isoleucine, phenylalanine tryptophan, lysine, arginine, histidine, aspartate, glutamate, asparagine, glutamine, cysteine and methionine. Particularly preferred esters are glycinate esters. These esters are prodrugs which are converted to the camptothecin compound by hydrolysis of the ester bond;

D

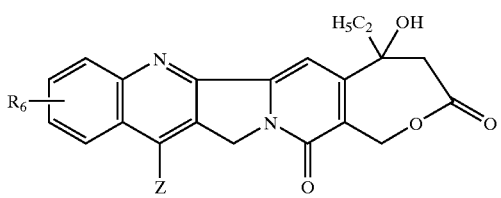

wherein Z is H, $C_{1-8}$ alkyl, trimethylsilyl, tertbutyldimethylsilyl, trimethylsilylmethyl, trimethylsilymethylaminomethyl, t-butyldimethylsilylethyl, trimethylsilylethyl,

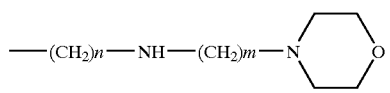

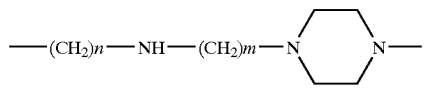

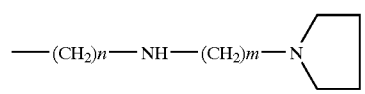

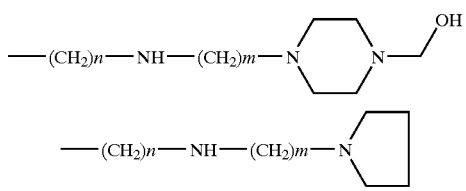

n=1–8: m=0–6 or $CH_2NR^1R^2$ where (a) $R^1$ and $R^2$ are, independently, hydrogen, $C_{1-6}$alkyl, $C_{3-7}$cycloalkyl, $C_{3-7}$ cycloalkyl-$C_{2-6}$ alkenyl, hydroxy-$C_{1-6}$ alkyl, $C_{1-6}$ alkoxy $C_{1-6}$ alkyl, 5,6, 7-membered heterocyclic rings contains one or more O, N, S (b)$R^1$ is hydrogen, $C_{1-6}$ alkyl, $C_{3-7}$cycloalkyl, $C_{3-7}$cycloalkyl-$C_{1-6}$ alkyl, $C_{2-6}$ alkenyl, hydroxy-$C_{1-6}$ alkyl or $C_{1-6}$ alkoxy-$C_{1-6}$ alkyl and $R^2$ is —$COR^3$ where $R^2$ is hydrogen, $C_{1-6}$ alkyl, perhalo-$C_{1-6}$ alkyl, $C_{3-7}$ cycloalkyl, $C_{3-7}$ cycloalkyl-$C_{1-6}$ alkyl $C_{2-6}$alkenyl, hydroxy-$C_{1-6}$ alkyl, $C_{3-7}$ alkoxy, $C_{1-6}$ alkoxy-$C_{1-6}$alkyl, or (c) $R^1$ and $R^2$ taken together with the nitrogen atom to which they are attached form a saturated 3–7 membered heterocyclic ring, which may contain a O, S or $NR^4$ group, where $R^1$ is hydrogen, $C_{1-6}$ alkyl, perhalo-$C_{1-6}$ alkyl, aryl, aryl substituted with one or more groups selected from the group consisting of $C_{1-6}$ alkyl, halogen, nitro, amino, $C_{1-6}$ alkylamino, perhalo-$C_{1-6}$alkyl, hydroxy-$C_{1-6}$ alkyl, $C_{1-6}$ alkoxy, $C_{1-6}$ alkoxy $C_{1-6}$ alkyl and —$COR^5$ where $R^5$ is hydrogen, $C_{1-6}$ alkyl, perhalo-$C_1$-6 alkyl, $C_{1-6}$ alkoxy, aryl, and aryl substituted with one or more $C_{1-6}$ alkyl, perhalo-$C_1$-6 alkyl, hydroxy-$C_1$-6alkyl, or $C_1$-6 alkoxy-$C_1$-6 alkyl groups. In the structure shown above, n is an integer of 1 or 2. Preferred aryl groups are phenyl and naphthyl;

E

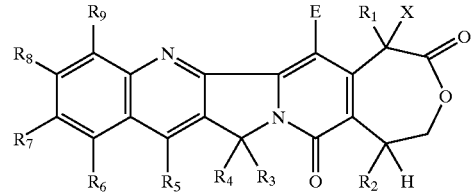

wherein E is H, $CO_2R$, $CONH_2$, CONHR, $CONR^2$, acyl, or CN; X is H, OH, or OR; $R^1$, $R^2$,$R^3$, and $R^4$ are independently the same or different and are H, linear or branched alkyl, linear or branched alkylaryl, hydroxyalkyl, or aryl; $R^5$, $R^6$,$R^7$,$R^8$, and $R^9$ are independently the same or different and are H, linear or branched alkyl, linear or branched alkylaryl, aryl, $CO_2R$, alkoxy, aryloxy, hydroxyalkyl, C-glycal, nitro, cyano, aminoalkoxy, Cl, F, Br, I, $SR^{10}$, $NR^{11}R^{12}$, or $OR^{12}$; is H, alkyl, aryl, alkylaryl, hydroxyalkyl or hydroxyalkyl; $R^{10}$, $R^{11}$, and $R^{12}$ are independently the same or different and are H, alkyl, aryl: alkylaryl, hydroxyalkyl, or acyl; $R^{13}$ is glycosyl;

F

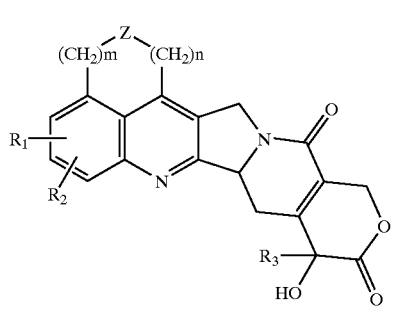

wherein $R^1$ and $R^2$ independently represent hydrogen atoms, hydroxyl groups, $C_{1-6}$ alkyl groups, $C_{2-6}$ alkenyl groups, $C_{2-6}$, alkynyl groups, $C_{1-6}$ alkoxyl groups, $C_{1-6}$ aminoalkoxyl groups, halogen atoms, nitro groups, cyano groups, mercapto groups $C_{1-6}$ alkylthio groups, $C_{1-6}$ hydroxyalkyl groups, $C_{1-6}$ halogenoalkyl groups, $C_{1-6}$ cyanoalkyl groups, $C_{1-6}$ nitroalkyl groups, $C_{1-6}$ aminoalkyl groups which may contain protective groups or $C_{1-6}$ alkyl groups, $C_{1-6}$ aminoalkylamino groups which may contain protective groups or $C_{1-6}$ alkylgroups at the amino-position heterocyclic $C_{1-6}$ alkyl groups which may contain $C_{1-6}$ alkyl, $C_{1-6}$ alkoxyl, amino, halogeno, nitro, or cyano groups, heterocyclic $C_{1-6}$ alkylamino groups, which may contain $C_{1-6}$ alkyl, $C_{1-6}$ alkoxyl, amino (which may contain protective groups), halogeno, nitro, cyano groups, or protective groups, amino-heterocyclic groups which may contain protective groups or $C_{1-6}$ alkyl groups at the nitrogen atom of the heterocyclic-amino groups which may, contain protective groups or $C_{1-6}$ alkyl groups at the nitrogen atom of the heterocyclic ring moiety or amino position, heterocyclic ring moiety or amino position, carbamoyl groups which may contain protective groups or $C_{1-6}$ alkyl groups, heterocyclic carbonyl groups which may contain $C_{1-6}$ alkyl, $C_{1-6}$ alkoxyl, amino, hydroxyl, halogeno, nitro, or cyano groups, $R^3$ represents an $C_{1-6}$ allyl group: Z represents O, S, CH —$R^4$ ($R^4$ stands for a hydrogen atom or a $C_{1-6}$ alkyl group), or N—$R^5$ ($R^5$ stands for a hydrogen atom, a $C_{1-6}$ alkyl group, or a protective group for the amino group), and m and n independently represent 0, 1 or 2; and

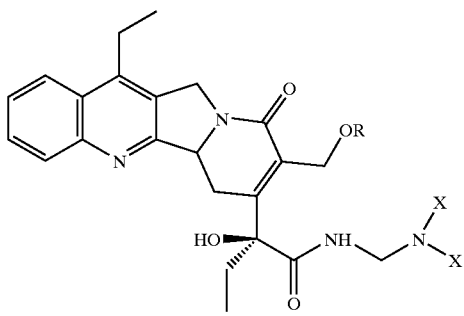

wherein X is a lower alkyl group, and R is a hydrogen atom or the grouping COY where Y is a linear or branched unsubstituted $C_1$–$C_{18}$ alkyl group; a lower alkyl group substituted by a halogen atom or a lower alkylthio, amino, acylamino, hydroxyl, lower alkoxy, aryloxy or lower alkoxycarbonyl group; a $C_3$–$C_{19}$ alkenyl, $C_3$–$C_{19}$ alkynyl or $C_3$–$C_8$ cycloalkyl group; a $C_3$–$C_8$ cycloalkyl group substituted by an acylamino-lower alkyl group; an N-acylpyrrolidyl group; a phenyl group; a phenyl group substituted by a halogen atom or a trifluoromethyl, nitro, amino, lower alkoxycarbonyl, lower alky, phenyl or lower alkoxy; a cinnamyl group; a benzyl group; a naphthyl group; a pyridyl group; a furyl group; or a thienyl group, as well as acid addition salts and quaternary ammonium salts.

Biodegradable and Nonbiodegradable Polymers

Controlled release biocompatible polymers and nonbiodegradable polymers have been employed for the local drug delivery. These vehicles have been used for contraception, insulin therapy, glaucoma treatment, asthma therapy, prevention of dental caries, and certain types of cancer chemotherapy. (Langer, R., and D. Wise, eds, *Medical Applications of Controlled Release*, Vol. I and II, Boca Raton, CRC Press (1986)). The novel-oligonulceotide-camptothecin drug complexes described herein can also be delivered to human and animals using the biodegradable and nonbiodegradable polymer systems that are already familiar to one skilled in that art. Utilization of polymer delivery systems for the novel camptothecin drug-DNA complexes described herein would allow for regional delivery of the therapy to the tumor site. Injectable, biodegradable polymeric systems and polymeric microstructures containing oligonucleotide-camptothecin drug complexes appear as attractive dosage forms to develop because they offer the possibilities of local regional therapy and minimization of systemic toxicities.

The polymer-based oligonucleotide-camptothecin drug dosage forms are designed in response to the following key factors: 1) a major obstacle for camptothecin drug delivery to target tissue is poor stability under physiological conditions (the α-hydroxy-δ-lactone ring functionality, upon which biological activity is critically dependent, hydrolyses extensively in human plasma with a $t_{1/2}$ value of 11 min and an almost negligible 0.2% lactone at equilibrium); 2) the drugs are S-phase specific and long-term, continuous exposure of a tumor is regarded to be more therapeutic than i.v. bolus administration where plasma drug levels rise and fall sharply; 3) systemic toxicities such as those observed when topotecan or CPT-11 are given intravenously can be mitigated. Local/regional administration of oligonucleotide-camptothecin drug complexes to tumors using injectable, biodegradable polymers and polymeric microstructures composed of either polymeric phospholipids or polylactide-co-glycolide is envisioned. Specific polymeric systems, among others, that can be utilized using for delivery of oligonucleotide-camptothecin drug complexes include: PEO-PLLA diblock copolymers composed of poly(ethylene oxide) (PEO) and poly(L-lactic acid) (PLLA); triblock copolymers (PEO-PLLA-PEO); blends of PEO-PLLA diblock copolymers and different PEOs; blends of PEO-PLLA-PEO triblock copolymers and different PEOs; and blends of poly(ε-caprolactone) (PCL) and poly(ethylene oxide) (PEO); and PEG-camptothecin constructs where the polymer is attached at the 7-position.

Drug-loaded polymeric systems can be utilized for long term, therapeutic treatment employing oligonucleotide-camptothecin drug complexes. By complexing the drug with oligonucleotides, added lactone ring stability for the drug is gained and the complex formation will also effect the controlled release of the drug and oligonucleotide from the polymer matrix into the target tissue. An important property of the polymeric device can include biodegradability; meaning that the polymer can break down or degrade within the body to non-toxic components after all drug has been released. Furthermore, techniques, procedures, and solvents used to fabricate the device and load the drug should be safe for the patient, prevent irritation to surrounding tissue, and be a harmless medium for the oligonucleotide-camptothecin drugs.

Currently, biodegradable implantable controlled release devices are fabricated from crystalline polymers of polyglycolic or polylactic acids. Due to the hydrophobic properties of these polymers, drug loading and device fabrication using this material requires organic solvents such as methylene chloride, chloroform, acetic acid or dimethyl formamide. Extensive drying is required after this process. In most cases, the final polymeric device is fabricated in a distinct solid shape (sphere, slab, rod, millicylinder) requiring surgical implantation.

The most widely investigated and advanced biodegradable polymers in regard to available toxicological and clinical data are the aliphatic poly($α_{—}$-hydroxy acids), such as poly(d,1- or 1-lactic acid) (PLA) and poly(glycolic acid) (PGA) and their copolymers. These polymers are commercially available and are presently being used as bioerodable sutures in surgery. These polymers could be used to deliver oligonucleotide-camptothecin drug complexes to the body.

A system for the controlled release of peptides, called Lupron Depot, is also based on lactic acid-glycolic acid copolymers. The Lupron Depot consists of injectable microcapsules, which release leuprolide acetate spanning a prolonged period (e.g., about 30 days) and the delivery system is used in the treatment of prostate cancer. Based on their extensive history of use, lactic acid-glycolic acid copolymers are logical choices for the delivery of oligonucleotide-camptothecin drug complexes to the body.

Other implantable delivery systems such as shown in Dunn et al, U.S. Pat. Nos. 4,938,763 and 5,278,202, can be used to deliver the -oligonucleotide-camptothecin drug complexes to the body. One unique aspect of these formulations is the fact that, when formulated, they maintain a liquid consistency which allows injection using standard 20-25 gauge needles. These polymers can be either thermoplastic or thermosetting. The thermoplastic system involves the forming of a polymeric solution in a suitable solvent and the polymeric solution is injected into the body. Upon exposure to body fluids or water, the solvent diffuses away from the polymer-drug mixture and water diffuses into the mixture where it coagulates. In this manner the polymer encapsulating the drug within the polymeric matrix solidifies. The thermoplastic solution requires the use of an organic solvent such as N-methyl-2-pyrrolidone, dimethylformamide, an alkyl ketone such as ethyl methyl ketone, propylene glycol, THF, DMSO, dodecylazacycloheptan-2-one (Azone) and the like.

Other polymer systems that can be used include the following: block copolymers composed of two different polymer blocks, i.e. hydrophilic poly(ethylene oxide) blocks and hydrophobic poly(propylene oxide) blocks. Such systems are synthesized to make up a triblock of poly(ethylene oxide)-poly(propylene oxide)-poly(ethylene oxide) and marketed under the Pluronic™ or Poloxamer™ tradenames. The triblock copolymers absorb water to form gels. These gels which can contain oligonucleotide-camptothecin drug complexes have the potential for use in topical pharmaceutical and cosmetic systems, i.e. in topical drug delivery systems. Surface-active block copolymers which exhibit reverse thermal gelation behavior and possess drug release characteristics can also be used.

Vitrification

The oligonucleotide-camptothecin drug complexes which are described herein can be conserved and prepared for entry to humans or animals using the process of vitrification. Using arrays of sugars and sugar-based alcohols, the complexes can be conserved. The sugars will vitrify, thereby conserving the oligonucleotide-camptothecin drug complex and preventing the dissociation of the drug from the complex in aqueous media and conserving the active lactone form of the drug. Sucrose, lactose, and raffinose are representative sugars that can be used in this vitrification process of oligonucleotide-camptothecin drug complexes.

The following examples are presented to further illustrate the invention, but it is not to be considered as limited thereto.

EXAMPLE 1

Camptosar (CPT-11) and Hycamtin (topotecan, TPT), shown in FIG. 1, are two clinically useful anticancer drugs of the camptothecin family which function by inhibiting human DNA topoisomerase I (TopoI) (Liu et al., 1996; Takimoto and Arbuck; 1996; Rowinsky et al., 1993). Successful inhibition of TopoI by camptothecins is known from structure-activity studies to require an intact lactone ring (ring E) functionality (Wani et al., 1987; Jaxel et al., 1989; Fassberg and Stella, 1992; Hertzberg et al., 1989). Unfortunately, this lactone moiety is subject to hydrolysis under physiological conditions, i.e. at pH 7 and above, with each camptothecin agent existing in equilibria with its corresponding ring-opened carboxylate form. The position of the equilibria is pH-dependent, with the carboxylate form predominating at physiological pH after 1 hr of incubation (Fassberg and Stella, 1992). Previous equilibrium dialysis studies which evaluated the interactions of extensively incubated (16 hrs) and hydrolyzed camptothecin with sonicated calf thymus DNA and plasmid DNA (2 mM base concentrations or less) provided little to no evidence of DNA binding (Hertzberg et al., 1989).

In this example, the effect of synthetic duplex DNA oligonucleotides on CPT-11 and TPT stability as a function of incubation time and DNA concentration using a combination of HPLC, UV, and NMR methods was investigated. Our studies demonstrate that the positively-charged and water-soluble TPT and CPT-11 congeners, as well as uncharged camptothecin, are capable of interacting directly with double-stranded DNA (dsDNA). Moreover, our results indicate that the dsDNA interactions of the camptothecin drugs of interest result in a marked stabilization of their active lactone forms.

In the absence of drug, TopoI mediates the relaxation of supercoiled DNA. TopoI first binds DNA and then nicks it on one strand, rotates the helix by one turn and finally rejoins the nicked strand (Liu et al., 1996; Henningfeld et al., 1996; Hertzberg et al, 1989). The nicking of DNA by TopoI creates a covalent intermediate in which the 3'-phosphate at the nick site is attached to the phenolic hydroxyl group of a tyrosine (Tyr723 in human TopoI). Camptothecin agents are thought to interact with this covalent intermediate at the nick site, thereby preventing the religation and ultimately leading to DNA fragmentation and cell death (Liu et al., 1989). As a result of intense study following their discovery as TopoI inhibitors, the camptothecins are now known to act through the formation of stable ternary complexes between drug, TopoI and DNA(Liu et al., 1989). However, strong evidence that these agents are capable of interacting directly with DNA in the absence of TopoI has not been previously identified.

Figure 2:
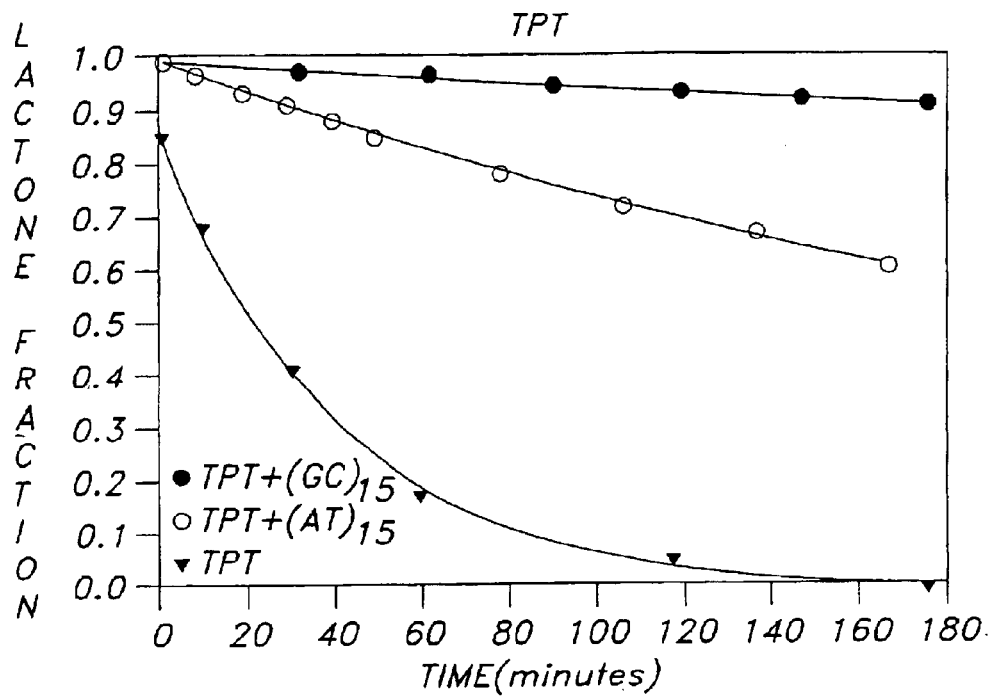
FIG. 2 represents a kinetic evaluation of the rate of lactone ring opening for topotecan (left panel) and CPT-11 (right panel) in the presence and absence of duplex DNA oligonucleotides ((dG-dC)$_5$ or (dA-dT)$_{15}$). Data for drug in the absence of DNA (triangles), drug in the presence of (dG-dC)$_{15}$ (solid circles) or (dA-dT)$_{15}$ (open circles) are shown. All experiments were conducted in phosphate buffered saline (PBS) (pH 7.40±0.05) at room temperature. Drug and DNA concentrations of 10 $\mu$M and ~30 mM base, respectively, were employed. Each profile represents the average of at least three independent kinetic runs with the same sampling schedules. The standard deviation of each point was typically 5% or less. Kinetic parameters for the various samples are summarized in Table 1.
Figure 2:
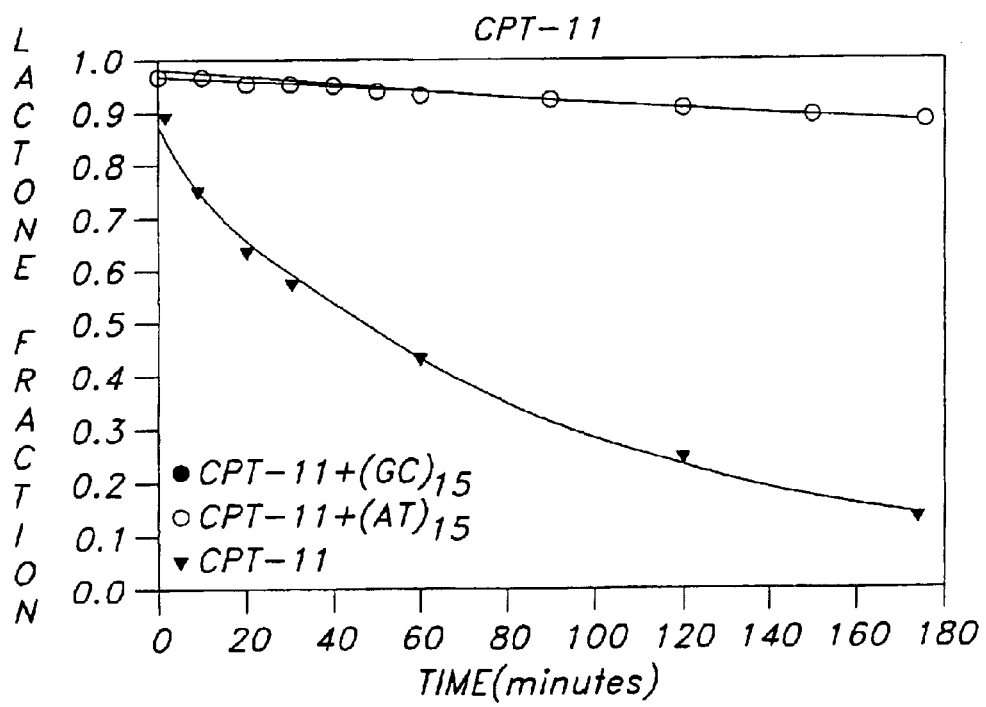

The impact of two different 30mer dsDNA oligonucleotides. $(dA-dT)_{15}$ and $(dG-dC)_{15}$ on drug stability in phosphate-buffered saline (PBS) solution at pH 7.4 and room temperature is depicted in FIG. 2. A reversed-phase HPLC assay was employed to assess the rate of hydrolysis and quantify the proportion of the lactone and carboxylate forms at equilibrium. In the absence of DNA, 10 $\mu$M samples of CPT-11 and TPT incubated for 3 hours and hydrolyzed with pseudo first-order kinetics displayed percent lactone at equilibrium values of 24% and 12%, respectively. The extent of lactone ring opening for both agents was markedly reduced, however, in the presence of dsDNA (~30 mM base concentration). Lactone levels for CPT-11 remained at 95% following three hours of incubation in the presence of $(dA-dT)_{15}$ or $(dG-dC)_{15}$ and at levels of 78% and 95%, respectively, for TPT. Even for time points out to 5 days, lactone levels remained high (50–60%) in the presence of DNA for both agents. Experiments conducted with 10 FM camptothecin demonstrated that the lactone form of this agent was also efficiently stabilized by the presence of ~30 mM base $(dG-dC)_{15}$ with lactone levels remaining above 80% after 3 hr.

Figure 3:
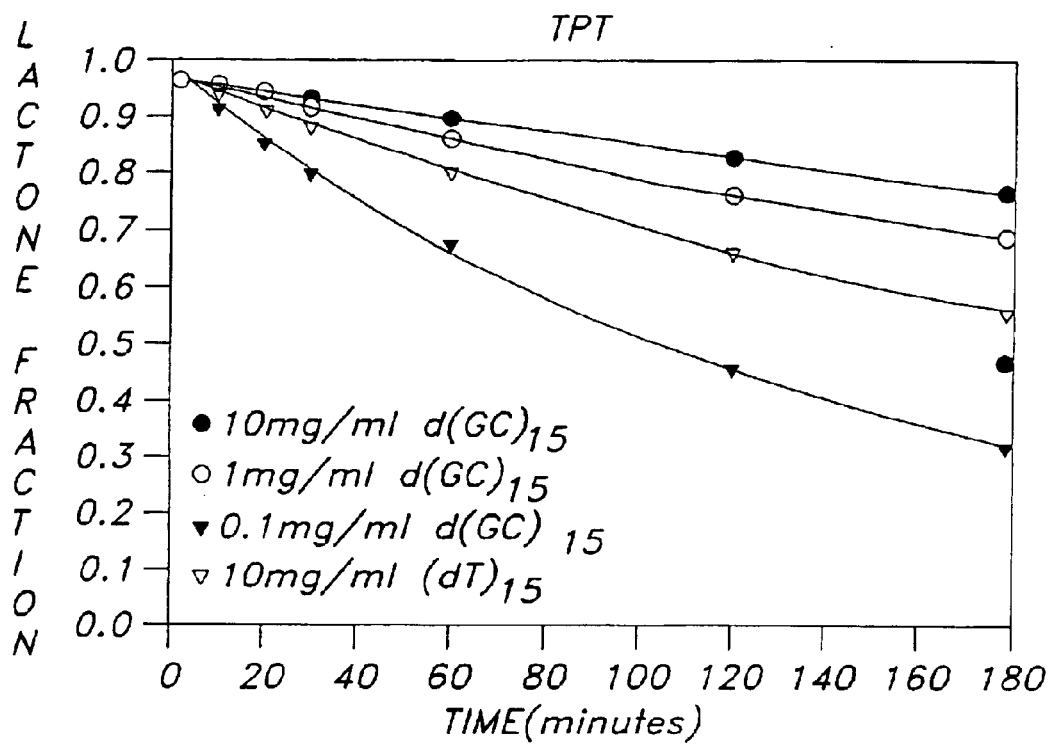
FIG. 3 represents a kinetic evaluation of the rate of lactone ring opening for topotecan and CPT-11 in the presence of various concentrations of duplex DNA oligonucleotides (GC$_{15}$ and AT$_{15}$) and single-strand DNA (dT)$_{30}$. All experiments were conducted in PBS (pH 7.40±0.05) at room temperature. Drug concentrations of 10 $\mu$M and DNA concentrations of 30 mM base for dsDNA and 33 mM base for ssDNA (dT)$_{30}$ were employed. Each profile represents the average of at least three independent kinetic runs with the same sampling schedules. The standard deviation for each point is typically 5% or less. Standard deviations in the kinetic results when using different DNA synthetic batches can range up to 10%. Kinetic parameters for the various samples are summarized in Table 1.
Figure 3:
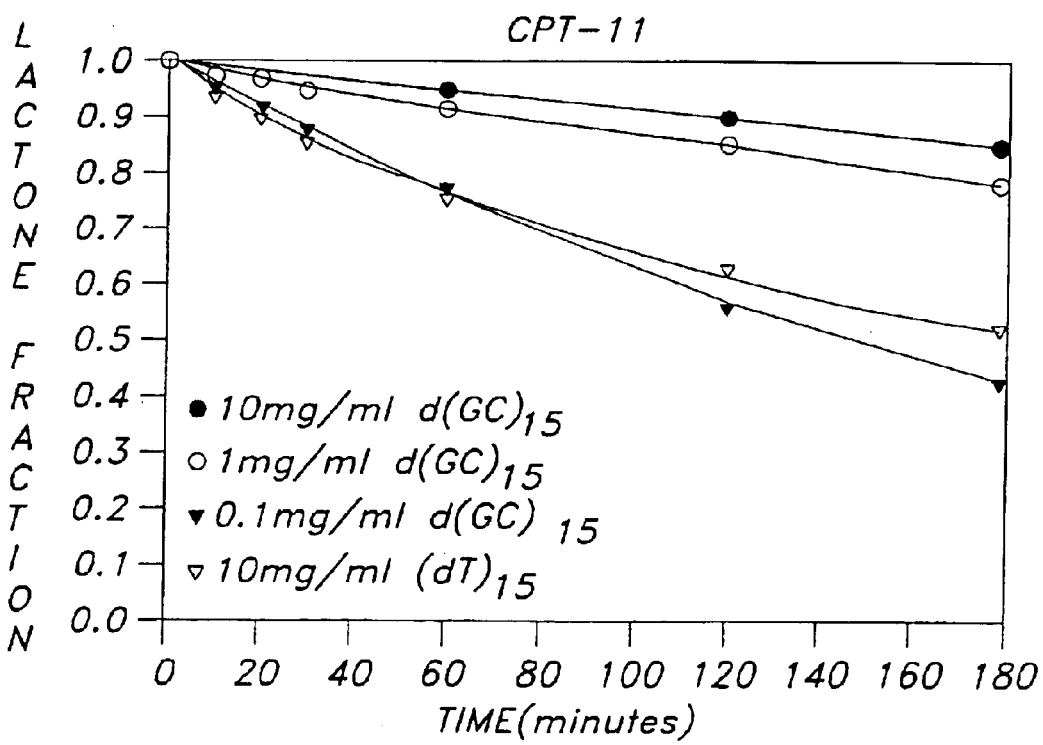
Figure 4:
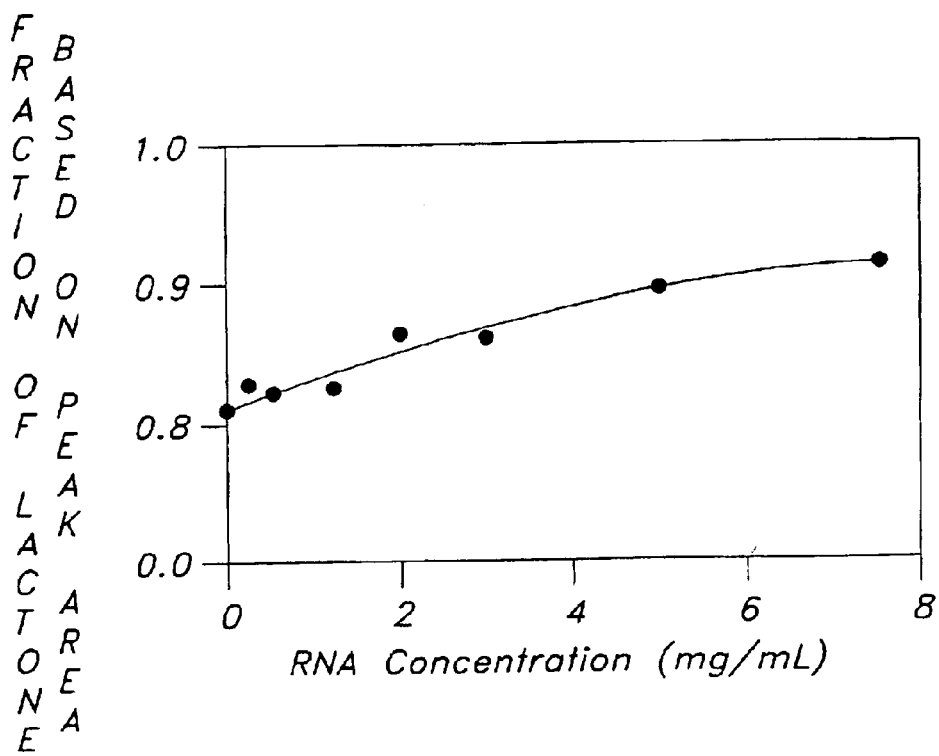
FIG. 4 depicts the stability of topotecan in the presence of various concentrations of RNA at 22° C. In these experiments, topotecan (at a final concentration of 1 $\mu$M) was incubated in PBS, pH 7.4 in the presence of various concentrations of RNA (total RNA from yeast) for 30 min at 22° C. and analyzed for the fraction of lactone present by reversed-phase HPLC. The figure indicates that the presence of RNA provides a means of enhancing the amount of active lactone form of the drug. As an example, in the presence of 7.5 mg/ml of RNA there exists a 10% greater amount of the lactone form than found in the absence of RNA.
Figure 5:
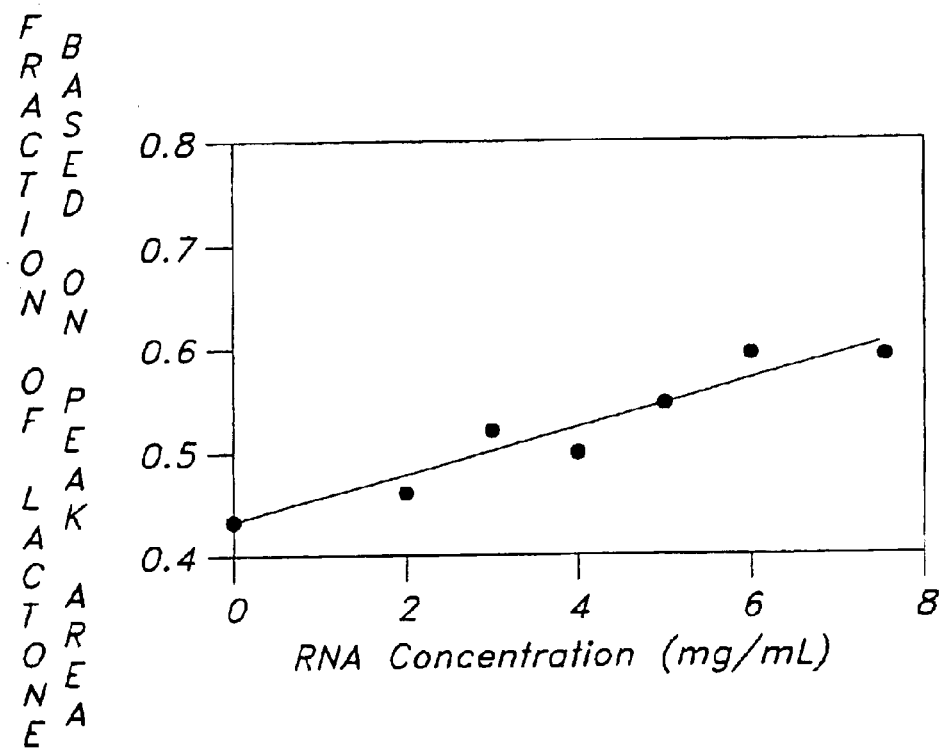
FIG. 5. Stability of topotecan in the presence of various concentrations of RNA at 37° C. Topotecan (1 $\mu$M final concentration) was incubated in PBS, pH 7.4 in the presence of various concentrations of RNA (total RNA from yeast) for 30 min at 37° C. and analyzed for the fraction of lactone present by reversed-phase HPLC. At a RNA concentration of 7.5 mg/ml, 12% more of the lactone form of topotecan is present.
Figure 6:
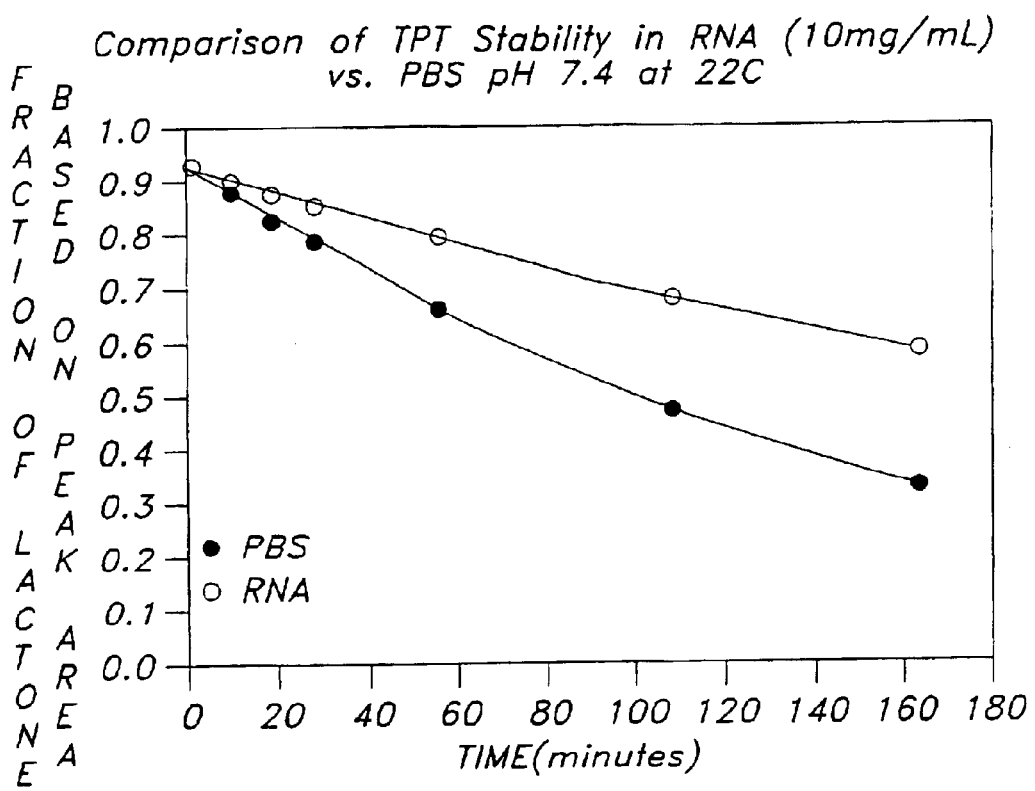
FIG. 6 represents a comparison of the stability of topotecan in the presence and absence of RNA at 22° C. Topotecan (1 $\mu$M final concentration) was incubated in PBS, pH 7.4 either alone (filled circles) or in the presence of 10 mg/ml of RNA (open circles) at 22° C. and analyzed for the fraction of lactone present at different times by reversed-phase HPLC. The figure indicates that in the presence of 10 mg/ml of RNA, 25% more of the lactone form of topotecan is present after 3 hrs.
Figure 7:
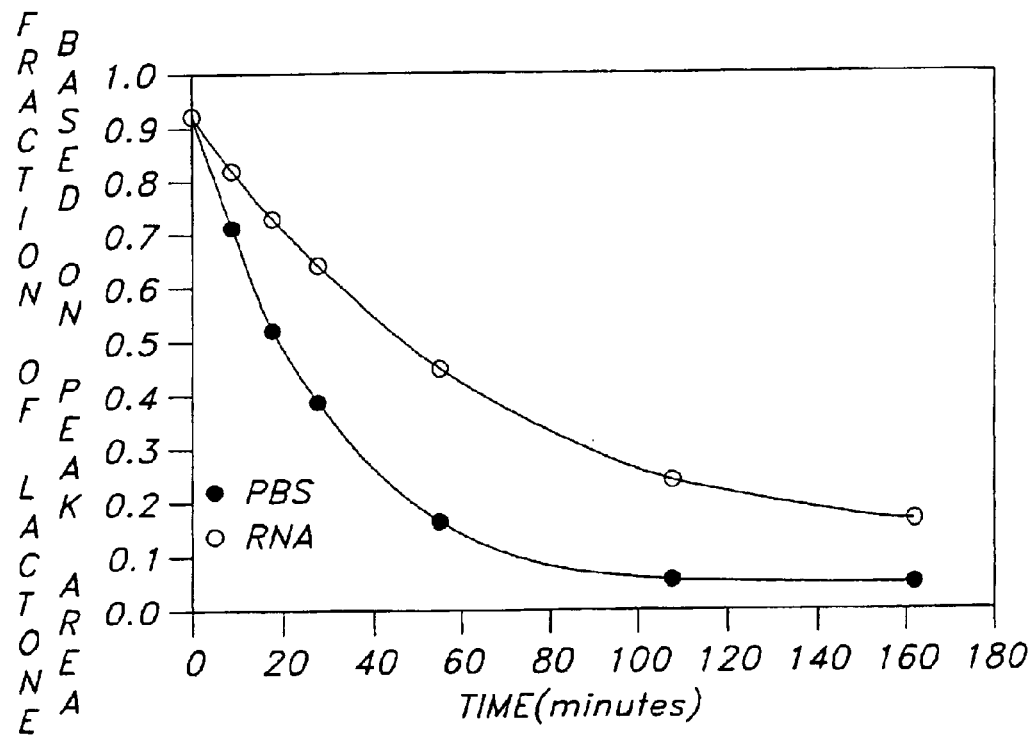
FIG. 7 represents a comparison of the stability of topotecan in the presence and absence of RNA at 37° C. Topotecan (1 $\mu$M final concentration) was incubated in PBS, pH 7.4 either in the absence (filled circles) or in the presence of 10 mg/ml of RNA (open circles) at 37° C. and analyzed for the fraction of lactone present at different times by reversed-phase HPLC. The figure indicates that in the presence of 10 mg/ml of RNA, 15% more of the lactone form of topotecan is present after 3 hrs.
Figure 8:
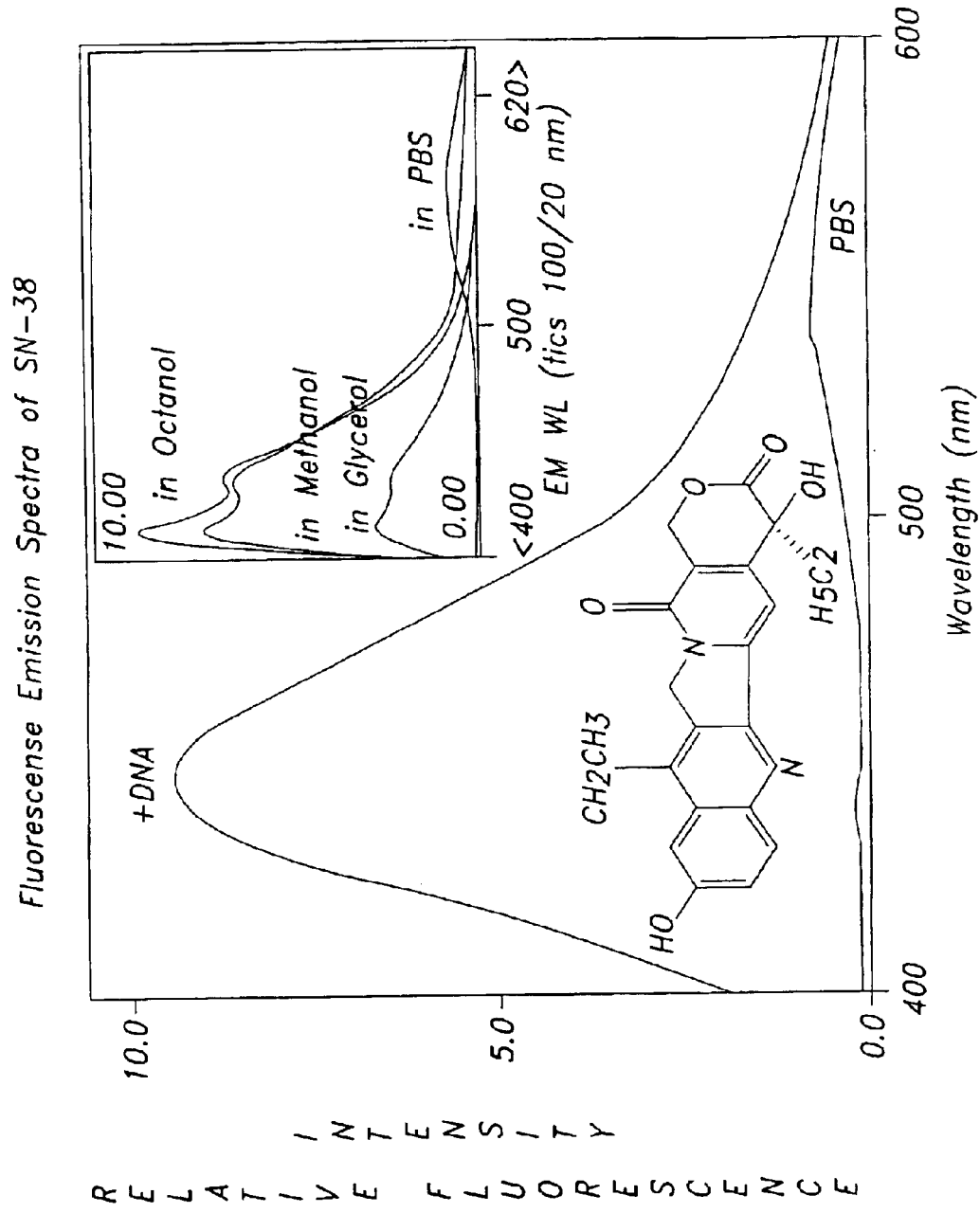
FIG. 8 depicts the marked shifting of the fluorescence emission spectra of SN-38 lactone (1 $\mu$M final concentration) in the presence of double-stranded DNA (dsDNA). SN38 contains a 10-hydroxy-nctionality which results in the molecule having a fluorescence emission which is highly sensitive to the presence of water in the surrounding microenvironment. The inset of the figure shows the dramatic shifting of the fluorescence of the molecule when water is excluded from the microclimate of the fluorophore. Note how the agent fluoresces in the 410 nm to 460 nm region when water is not present, but fluoresces at 520 to 530 nm when water is present. Note how the fluorescence of SN38 lactone shifts markedly to lower wavelength upon interacting with double-stranded DNA, clearly indicating that the agent is capable of directly interacting with the DNA. These data indicate that by interacting with DNA, the fluorophore can relocate to different microenvironment with markedly reduced water content. The fluorophore was directly added to the DNA solution and the spectra recorded immediately (within 2 min.) prior to any significant conversion of the agent to carboxylate form.

Addition of pure carboxylate forms of CPT-11 and TPT to ~30 mM base dsDNA solutions in PBS followed by incubation at room temperature was found to result in relactonization and the promotion of high levels of active lactone (~30% after 30 hrs). HPLC analyses were also completed on solutions containing single-strand DNA (ssDNA) in the form of ~33 mM base $(dT)_{30}$ (see FIG. 3). Stability equilibrium and kinetic parameters are summarized in Table 1.

TABLE 1

Summary of the Kinetic and Equilibrium Parameters for the Hydrolysis of 10 uM Topotecan and CPT-11 in the absense and presence of dsDNA oligonuclectides $(dG-dC)_{15}$ and $(dA-dT)_{15}$ at Room Temperature and 37° C.[a]

| Drug | Samples | Temperature (° C.) | Half-lives[b] (min) | % Lactose at Equilibrium[b] |
|---|---|---|---|---|
| TPT | PBS buffer | 22 | 59.6 ± 2.0 | 15 ± 1 |
|  | $(DG-dC)_{15}$ | 22 | >3 days | ~50% |
|  | $(DA-dT)_{15}$ | 22 | >d days | ~50% |
|  | PBS buffer | 37 | 28.5 ± 1.0 | 10 ± 1 |
|  | $(DG-dC)_{15}$ | 37 | 89.0 ± 2.0 | 26 ± 2 |
|  | $(DA-dT)_{15}$ | 37 | 71.2 ± 2.0 | 19 ± 2 |
| CPT-11 | PBS buffer | 22 | 54.8 ± 2.0 | 17 ± 1 |
|  | $(DG-dC)_{15}$ | 22 | >3 days | ~50% |
|  | $(DA-dT)_{15}$ | 22 | >3 days | ~50% |
|  | PBS buffer | 37 | 20.2 ± 1.0 | 8 ± 2 |
|  | $(DG-dC)_{15}$ | 37 | 46.7 ± 2.0 | 30 ± 2 |
|  | $(DA-dT)_{15}$ | 37 | 65.3 ± 2.0 | 29 ± 2 |

TABLE 1-continued

Summary of the Kinetic and Equilibrium Parameters for the Hydrolysis of 10 uM Topotecan and CPT-11 in the absense and presence of dsDNA oligonuclectides (dG-dC)$_{15}$ and (dA-dT)$_{15}$ at Room Temperature and 37° C.[a]

| Drug | Samples | Temperature (° C.) | Half-lives[b] (min) | % Lactose at Equilibrium[b] |
|------|---------|--------|-----------|---------------|

[a]Hydrolysis of drugs was monitored using HPLC assay (Burke & Mi, 1994). All samples were at pH 7.4 ± 0.05. Data are expressed as the mean ± SD (n = 3).
[b]The half-lives $t_{1/2}$ and percent lactone at equilibrium values were determined from decay profiles (FIG. 2). A $t_{1/2}$ value = 0.694/$K_t$, where $K_t$ is the pseudo-first-order hydrolysis rate constant recovered by nonlinear least squares analysis as described previously (Burke & Mi, 1994).

Note how the presence of DNA markedly stabilizes the biologically-active form of the camptothecins drugs. Samples containing ssDNA showed significantly diminished effects on stabilizing both TPT and CPT-11, with dsDNA solutions some 10- to 100-fold more dilute than the (dT)$_{30}$ solutions affording approximately equal lactone stabilization. But it is clear from our work that camptothecin drugs can interact with ssDNA as well as RNA (see FIGS. 4 through 7) and these interactions stabilize the biologically-active lactone forms of these agents.

To gain mechanistic insight into why the stabilization occurs, fluorescence spectroscopic scans of SN-38 lactone in the presence and absence of DNA were recorded. Upon introduction of DNA into solution, a very prominent spectral shift is immediately discerned indicating that the lactone form of SN-38 binds the DNA. Thus, direct binding information indicates that the lactone forms of camptothecin drugs bind DNA which explains why higher levels of lactone drug are observed in solution when DNA is present.

Figure 9:
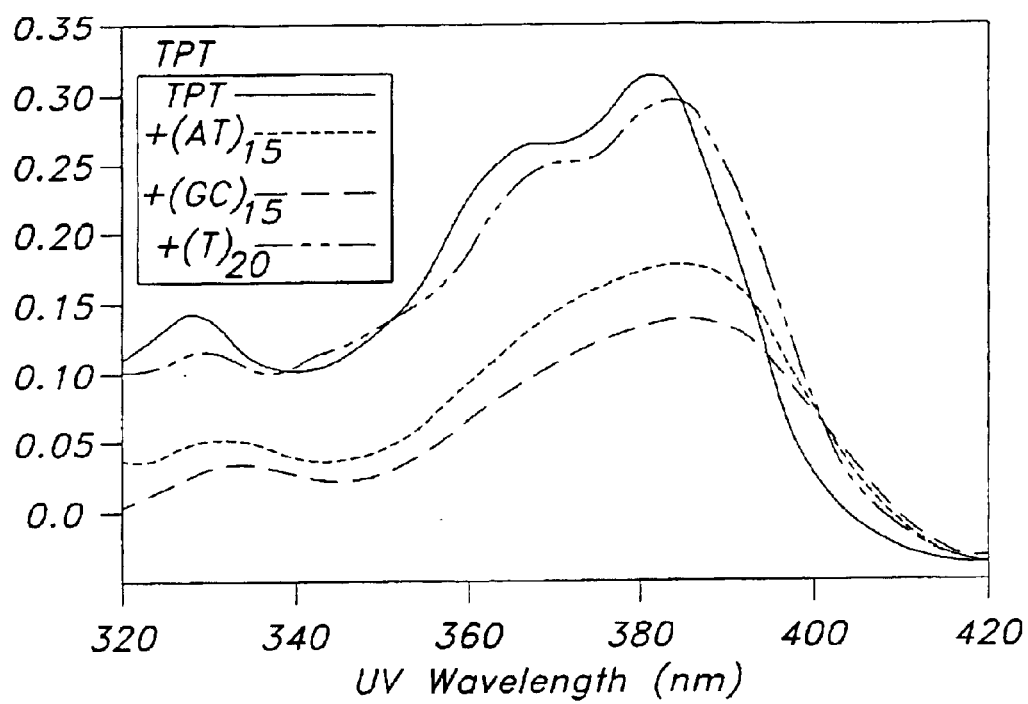
FIG. 9 shows the UV absorption spectra of topotecan lactone (left panel) and CPT-11 lactone (right panel) in the absence and presence of duplex DNA oligonucleotides ((dG-dC)$_{15}$ or (dA-dT)$_{15}$) in PBS (pH 5.00±0.05 at room temperature). Drug, (dG-dC)$_{15}$, and (dA-dT)$_{15}$ concentrations of 10 $\mu$M, 16 mM base, and 24 mM base, respectively, were employed.
Figure 9:
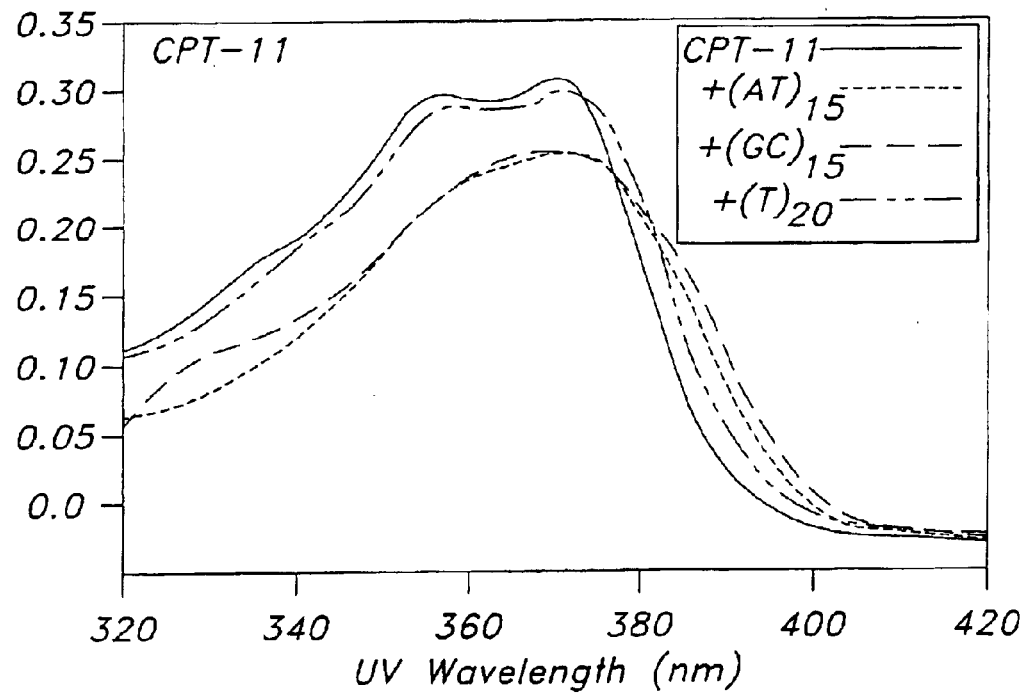

FIG. 9 depicts changes in the UV spectra of the lactone forms of CPT-11 and TPT in PBS (pH 5) following addition of the (dA-dT)$_{15}$ or (dG-dC)$_{15}$ 30-mers. Note the substantial hypochromic and red spectral shift observed for both drugs in the presence of DNA is suggestive of a possible intercalation mode of binding. Consistent with the HPLC data, the UV data also provides evidence that TPT displays a sequence preference of (dG-dC)$_{15}$ over (dA-dT)$_{15}$, while no signs of any sequence preference were observed for CPT-11. A stronger hypochromic effect shift in the UV spectra of TPT in the presence of (dG-dC)$_{15}$ vs. (dA-dT)$_{15}$ is consistent with a stronger interaction with the former, albeit differences in transition state dipole interactions could also account for the observed effect.

Figure 10:
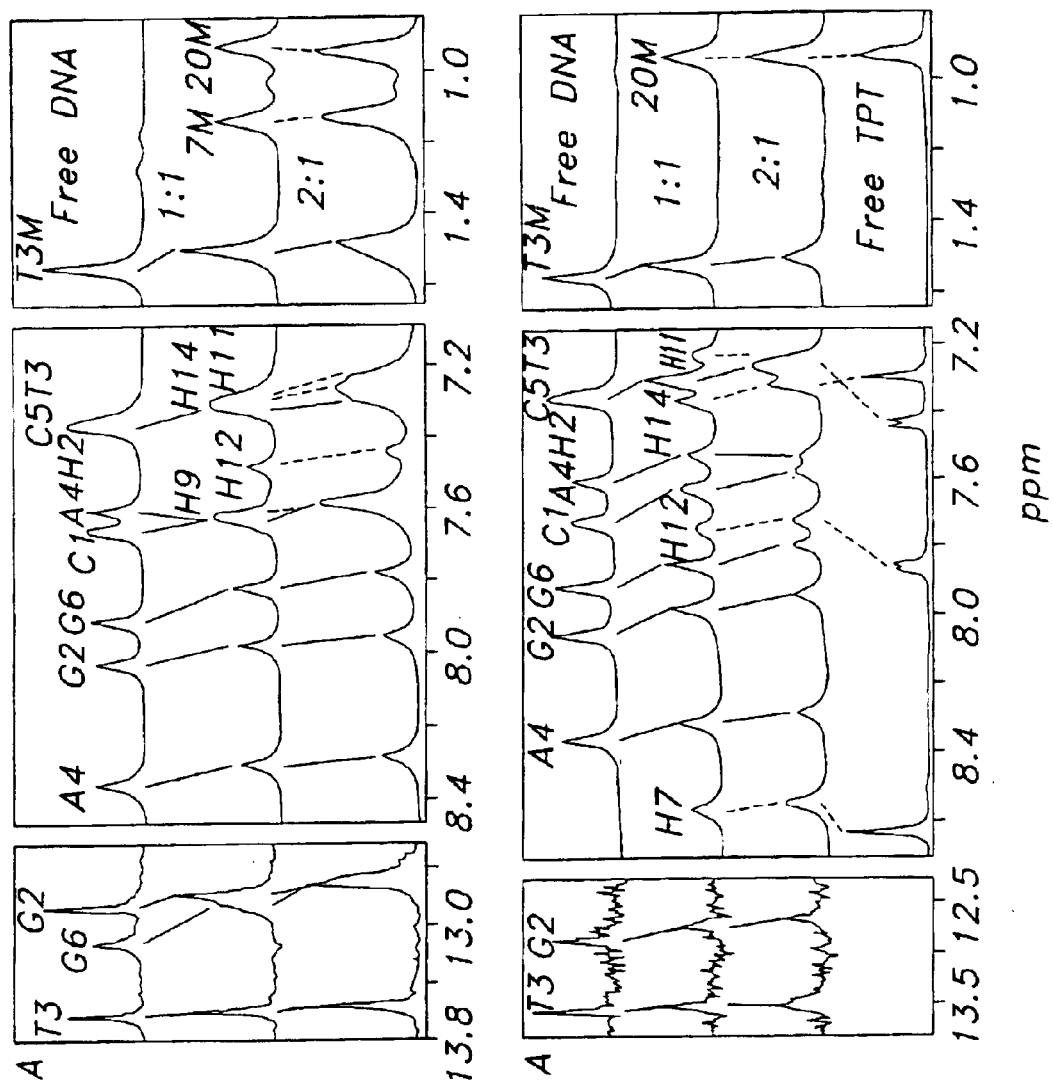
FIG. 10 shows NMR spectra depicting the titration of (A) CPT-11 to d(CGTACG) at pH 7.0, 20° C. and (B) TPT lactone to d(CGTACG) at pH 5 at 20° C. The ratios shown in the figure are for drug/DNA.
Figure 11:
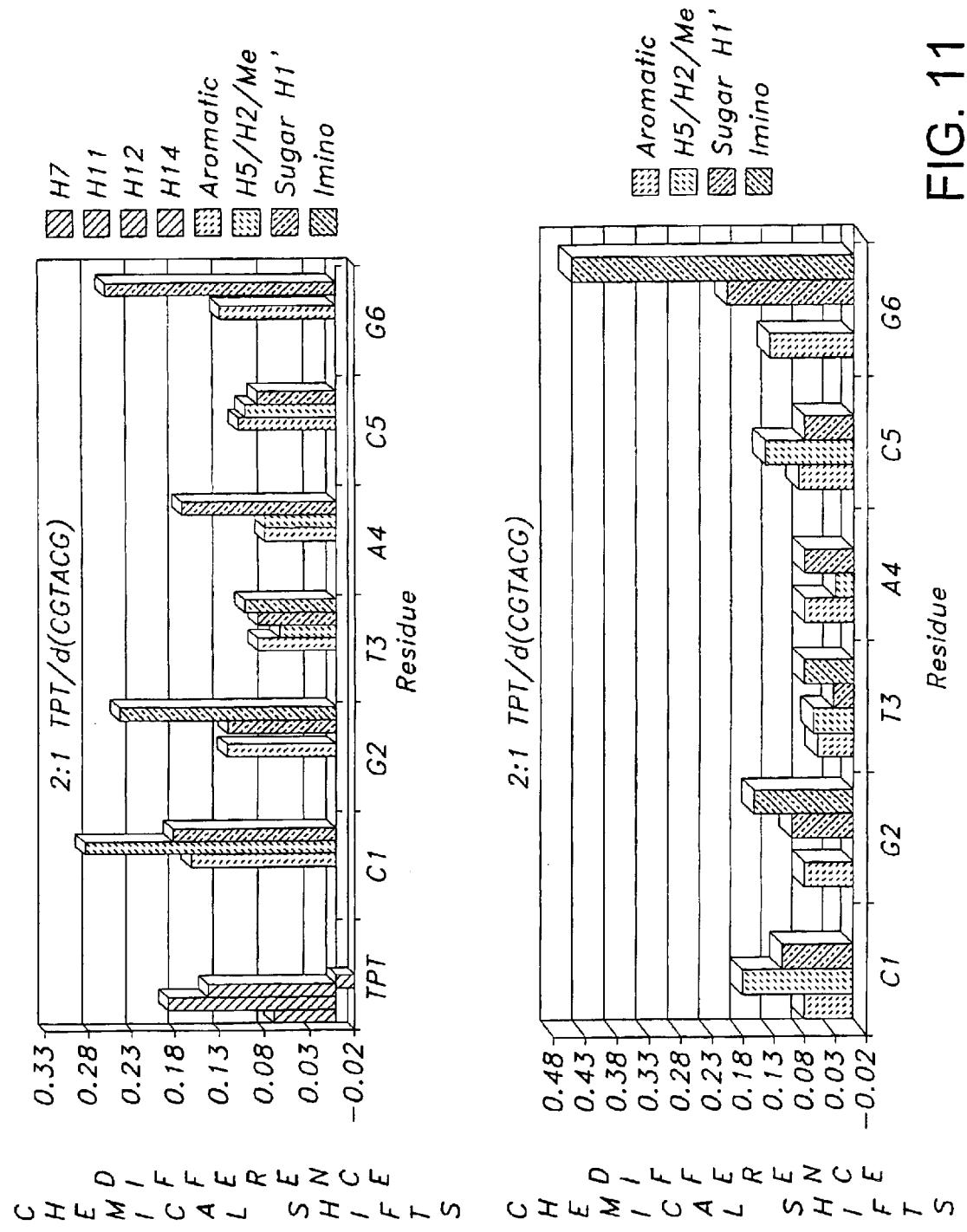
FIG. 11 contrasts the changes in the $^1$H NMR resonances for both free drug and nascent DNA versus 2:1 drug DNA complexes. Not how the chemical resonances of both the drug and DNA shift upfield upon complex formation.

Further insight into the molecular interactions between CPT-11 and TPT with dsDNA oligonucleotide d(CGTACG) was obtained from NMR studies. FIGS. 10 and 11 shows that addition of the drugs to DNA at increasing ratios resulted in up-field shifts of the DNA resonances, especially for the imino resonances G2 and G6. The drug resonances also shifted up-field in a correlated fashion. In the case of TPT, the aromatic resonances of H7, H12, H 11 protons shifted from 8.62, 7.87 and 7.43 ppm to 8.55, 7.73 and 7.24 ppm, respectively. Such up-field shifts of both DNA and drug resonances are characteristic of an intercalative mode of drug binding (Feigon et al., 1984; Wang, 1992).

The unequivocal assignments of the resonances associated with the lactone/carboxylate forms (FIG. 10) also allow us to confirm the stabilizing effect which DNA elicits on the lactone form of each agent. Additional 2D-NOESY experiments were also completed for both CPT-11 and TPT complexed to d(CGTACG) at different drug:DNA ratios of 1:1, 2:1, and 3:1 and the evidence is clearly consistent with drug binding to DNA. The 20-methyl resonances of CPT-11 lactone occur at 0.95 ppm, which changes to 1.06 ppm (20 M) upon the formation of opened-ring species. The NMR time course studies of CPT-11 and TPT concerning the differential rates of ring opening in the presence and absence of d(CGTACG) were consistent with determinations made using the HPLC method.

In summary, we have shown that the active lactone forms of CPT-11 and TPT are stabilized through interactions with dsDNA We have shown using high sensitivity fluorescence spectroscopic measurements that SN-38 lactone can directly bind to DNA, indicating that direct binding of lactone occurs which explains the effects of the presence of DNA on the lactone-carboxylate equilibria. The presence of dsDNA, in fact, was found to promote the conversion of inactive carboxylate to active lactone. Our results thus provide the first evidence that duplex DNA devoid of TopoI may play a functional role in the biological activities of the camptothecin drugs through the promotion of active lactone levels within the cell nucleus. These results suggest that the camptothecin drugs, upon reaching chromosomal DNA, may interact directly with DNA prior to the action by TopoI (although the site of drug binding to DNA is not necessarily at the site of topoisomerase 1 action). The DNA-associated drugs are likely to be in their active lactone forms and ready for the subsequent drug-DNA-enzyme complex formation.

EXAMPLE 2

Camptothecin Drug-DNA Complexes in Solution

Camptothecin drugs reversibly complexed to synthetic oligonucleotides in their lactones forms were produced in phosphate-buffered-saline using the following procedure. The Phosphate-buffered saline (PBS) buffer contained 8 mM Na$_2$HPO$_4$, 1 mM KH$_2$PO$_4$, 137 mM NaCl and 3 mM KCl (pH 7.4). The oligonucleotides d(CGTACG) were synthesized on an automated DNA synthesizer at the Genetic Facility of University of Illinois at Urbana Champaign. In addition, (dG-dC)$_{15}$ and (dA-dT)$_{15}$ were purchased from IDT (Coralville, Iowa). The CPT-11 used in the study was generously provided by Yakult (Tokyo) and topotecan (TPT) was obtained from the National Cancer Institute. The drug lactone stock solutions were prepared in aqueous solution at 2 mM, pH 5. Solutions of drug-DNA complexes were prepared by mixing the appropriate amounts of drug stock solution and DNA stock solution in PBS, followed by pH adjustment to the desired value. Drug-DNA complexes solutions were vacuum-dried in a SpeedVac at room temperature, and then dissolved in 0.5 ml 99.8% D$_2$O for 1D $^1$H NMR spectra; or in 0.5 ml 90% H$_2$O/10%/D$_2$O for 1D H$_2$O spectra. The final DNA duplex concentrations ranged between 0.7 to 1 mM for all 1D NMR spectra. 1D H$_2$O NMR spectra were collected using the 1-1 pulse sequence (Sklenar, V.; Brooks, B. R.; Zon, G.; Bax, A. FEBS Lett 1996, 216, 249–252). The NMR spectra were recorded on a Varian VXR500 (University of Illinois, Urbana, Ill.) and Varian Inova 500 (University of Kentucky, Lexington, Ky.) 500 MHz spectrometers. The chemical shifts (in ppm) were referenced to the HDO peak which was calibrated to a 2,2-dimethyl-2-silapentane-5-sulfonate (DSS) external standard at different temperatures. The NMR data were processed with the program FELIX v. 1.1 (Hare Research, Woodinville, Wash.) or FELIX 95.0 (MSI) on Silicon Graphics workstations. The UV spectrum of a drug-DNA complex was obtained by subtracting the spectrum of free DNA from the spectrum of the complex. The hydrolysis kinetics of both drugs were determined by the quantitative reversed-phase high-performance liquid chromatographic (HPLC) methods as decribed previously [Mi, Z.; Malak, H.; Burke, T. G. *Biochemistry* 1995, 34, 13722–13728; Warner, D. L.; Burke, T. G. *J. Chromatogr. B* 1997, 691, 161–171]. DNA stock solutions were prepared by dissolving the oligos in PBS at a concentration of ~30 mM base concentration, with adjustment of pH to 7.4. 5 µg1 of 1 mM drug stock solutions (either lactone form or carboxylate form) were then added to 0.5 ml pH 7.4 PBS or DNA stock solutions and assayed by HPLC to determine lactone stability or relactonization parameters, respectively. We observed a stronger hypochromic effect shift in the UV spectra of TPT in the presence of $(dG-dC)_{15}$ vs. $(dA-dT)_{15}$ is consistent with a stronger interaction with the former, albeit differences in transition state dipole interactions could also account for the observed effect. 2D-NOESY experiments were also completed for both CPT-11 and TPT complexed to d(CGTACG) at different drug:DNA ratios of 1:1, 2:1, and 3:1. The drug-DNA complexes formed in this manner could be delivered in a number of different manners.

EXAMPLE 3

Preparation of Polyetheyleneglycol-modified Cationic Liposomal Formulations Containing Oligonucleotide-topotecan Complexes.

Liposomes containing cationic DMRIE, DOPE, distearoylphospatidylcholine:cholesterol (5:5:60:30) were prepared by repeated freeze-thawing followed by extrusion through 50 nm pore membranes as previously described (Papahadjopoulos, D. *Biochim. Biophys. Acta* 1997, 557, 19–23; Papahadjopoulos, D. *J. Biol. Chem.* 1998, 273, 15621–15627). The procedure provided the total lipid concentration 1 mg/ml. The liposomal DNA (5'-tct-ccc-agc-gtg-cgc-cat-3')-topotecan complex were produced by overnight incubation of liposomes with the DNA-Topotecan complex (10 µg) in PBS at 4° C. with gentle stirring. Nonencapsulated oligonucleotide and complex was removed using gel-exclusion chromatography on Sepharose B (Amersham Pharmacia Biotech). Particle size was determined by Malvern Zetasizer.

EXAMPLE 4

Preparation of cationic lipid DODAC, Non-cationic Lipid DMPC, Nucleic acid β-gal Plasmid, and Topotecan Formulations Using a Detergent Dialysis Method.

The detergent dialysis method described in U.S. Pat. No. 5,705,385 is used to prepare cationic lipid DODAC, non-cationic lipid DMPC, nucleic acid β-gal plasmid, and Topotecan formulations. To the sonicated solution of DMPC (160 mmoles in 200 mM OGP detergent) is added DNA-topotecan solution (10 µg of drug and 100 µg plasmid in 200 µL of 200 mM aqueous OGP detergent) and the mixture is allowed to incubate for 0.5 hr at room temperature. The DODAC solution (160 mmoles in 400 µL OGP) is added slowly to the DNA-topotecan-DMPC mixture while vortexing the mixture at low speed. The resultant mixture (1 mL) is dialyzed against six changes of 2 L of distilled sterile water over 36 hours. Size distribution of the complexes are determined using Malvern Zetasizer. Two populations of particles are anticipate, one group in the size range from 50 to 150 nm and the second population sized from 500 to 1000 nm.

EXAMPLE 5

Preparation DOTMA-DMPC Liposomes Containing DNA and Topotecan That Has Been Actively Loaded.

Liposomes are prepared by hydrating a DOTMA-DMPC film (dried down from $CHCl_3$ and placed under high vacuum for 12 h) in 300 mM citric acid buffer (pH 4.0) containing 50 µmol d(CGTACG) to achieve a final lipid concentration of 100 mg/ml. These MLVs containing DNA are frozen and thawed 5 times and extruded 5 times through polycarbonate filters with a pore size of 200 nm. The liposomes are then adjusted to pH 7.5 with 1.0M $Na_2CO_3$, and incubated with DNA-topotecan (10 mg lipid/ml) complex at 60° C. for 5 minutes. Unbonded complex is removed as described above by gel-exclusion chromatography on Sepharose B.

EXAMPLE 6

Phage DNA-GG211 Liposome Complexes.

A liposomal preparation which constitutional lipids are DSPC, DLPC, and cholesterol (molar ratio of 2:1:1 and entrapping DNA is prepared as described below). 0.2 µmol of DSPC and the other lipids are dissolved in chloroform and mixed in a conical test tube, the inner glass surface of which was previously treated with a silation agent. The chloroform solvent is then removed using a rotary evaporator of reduced pressure to form a lipid film (total lipid amount: 1 µmol). Complete removal of the trace residues of organic solvents was achieved by storing the vessel containing lipid film in a vacuum dessicator at 20° C. Then 1 mg of phage DNA in 300 µl of phosphate buffered saline (PBS, pH 7.4) containing 200 µM GG211 was added to the film and gently stirred. The resulting solution is gently agitated for 2 minutes with a vortex mixer to obtain DNA-GG211 entrapped in multilamellar lipid vesicles and lipid aggregates. DNA not entrapped by the liposomes is removed by utilizing a density gradient-centrifugal method with Ficoll-Paque (6 g Ficoll 400 and 9 g sodium diatrizoate in 120 ml, Ficoll 400 is a high molecular weight hydrophobic polymer of sucrose produced by copolymerizing sucrose with epichlorohydrin at elevated temperatures above 30° C.). An analysis by agarose gel electrophoresis of the DNA is useful to evaluate any possible change in DNA induced by the process. To alter the physical characteristics of the DNA-lipid-drug complexes, the samples are processed by utilizing a freeze-dry method or freeze-thawing method, as stated below.

EXAMPLE 7

Large Unilamellar Liposomes Containing The Highly Hydrophobic Camptothecin DB67 and Plasmid DNA.

Large unilamellar liposomes composed of plasmid DNA and the highly hydrophobic camptothecin 10-hydroxy-7-trimethylsilylcampotothecin are prepared using the method of Mok and Cullis, 1997 (Biophys. J. (1997) 73: 2534–2545), with modification. Mixtures of DOTMA, DOPE, and DMPC (1:1:1) are dispensed in chloroform and dried under a stream of nitrogen as continuous agitation of the sample with a vortex mixer occurs. The sample is then placed in a vacuum desiccator to remove any residue of trace organic solvents. The resulting films are hydrated with phosphate-buffered saline (PBS) and freeze-thawing of the sample occurs five times to produce homogeneous multilamellar vesicles (MLVs). This is followed by extruding these liposomal mixtures 20 times through double 100-nm pore size polycarbonate filters (Avestin, Toronto, CN) under nitrogen at a pressure of 400 to 450 psi. The size of the particles are checked by a Malvern Zetasizer. 40 µg Plasmid DNA (pCMVBgal is placed in 200 µl) and 200 µM DB67 is added using a DMSO stock of the drug such that DMSO concentration does not exceed 0.5%. The preformed cationic lipid suspension is added (200 µl) and the samples mixed together. The resulting mixture is incubated at room temperature for 15 min and then centrifuged at 12,000×g in a Sorvall MC microcentrifuge for 15 min.

EXAMPLE 8
Encapsulation of Camptothecins and Plasmid DNA in Liposomes and Cytotoxicity Studies in Cancer Cells Dipalmitoylphosphatidylcholine (DPPC), dioleoylphosphatidylglycerol (DOPG) and dioleoylphosphatidylethanolamine (DOPE) samples are obtained from Avanti Polar Lipid (Pelham, Ala.). DOTMA is synthesized as described previously (Felgner, P. L. et al., PNAS 84: 7413–7417 (1987)). DOPG/DOPC/DOPE/DOTMA/camptothecin/plasmid vesicles are prepared by first solvating 50 mg of DOPG and 50 mg of DOPC, 50 mg DOPE and 50 mg of DOTMA of interest in chloroform in a sonication vial and then drying the sample by removal of the solvent under a stream of nitrogen gas. The sample is then placed on a vacuum pump overnight. The sample is hydrated the following day with phosphate-buffered-saline to a concentration of 10 mg/ml total lipid. The phosphate-buffered saline (PBS) solution contains 8 mM $Na_2HPO_4$, 1 mM $KH_2PO_4$, 137 mM NaCl, and 3 mM KCl at a pH of 7.4. Following the hydration the liposomes are vortex mixed for 5–10 min at 55° C. Lipid suspensions are then sonicated using a bath-type sonicator from Laboratory Supplies Co., Hicksville, N.Y., for 34 hours until optical clarity is achieved. A decrease in pH of the final preparation is compensated for by the gradual addition of small amount of a 0.4 M NaOH solution in PBS such that the final pH is adjusted to 7.4. The liposome sample is then resonicated for 10 min. and then annealed at 55° C. for 30 min. Plasmid pUCSV2CAT (an oligonucleotide of approximately 5 kb) containing camptothecin drug complexed to the oligonucleotide is added to the liposomal preparation and the complexes then form. The DNA-lipid-camptothecin drug complexes are then evaluated for cytotoxicity studies in cell culture experiments. The complexes are added to cells and the complexes associate with the cell membrane and the complexes are internalized. Following internalization, the reversibly associated complexes dissociate and release active lactone forms of the camptothecin drugs in the cancer cells. The uncompleted drug is then free to diffuse into the nucleus of the cancer cells and inhibit the topoisomerase I target enzymes. Cytotoxicities of the oligonucleotide-lipid-camptothecin drug complexes are evaluated using the growth inhibition method. HL-60 cells ($5 \times 10^5$ cells/ml) are exposed continuously for 24 hr and 72 hr periods at 37° C. with 6–7 sequentially diluted drug concentrations. After treatment, aliquots of cells are mixed with an equal volume of 1.0 mg/ml solution of erythrocin B (Hay, 1992) and unstained, viable cells are counted with a hemacytometer. The percentage of viable cells are estimated by scoring 150–300 cells per sample.

EXAMPLE 9:
Antisense-Camptothecin Drug Formulations

Polynucleotide-complexes are prepared by taking 200 μM camptothecin drug stock solution in PBS and adding a hammerhead ribozyme at a 1:1 ratio. Lipid complexes of the above are then formed by preparing a mixture of 0.5 ml of a 10 μg/ml polynucleotidecamptothecin drug solution with 0.5 ml of sonicated DOTMA/PE or DOTAP/PE liposomes at 40–100 μg/ml by gradual mixing of the syringe contents at 39° C. As a result of this procedure positively-charged camptothecin drug: ribozyme complexes are obtained which spontaneously deliver polynucleotide and drug into cells in tissue culture. Different ratios of positively-charged liposomes to polynucleotides to drug can be used to suit particular needs.

Modifications and variations of the compositions of the present invention and methods for use will be obvious to those skilled in the art from the detailed description of DNA-oligonucleotide complexes which we have presented. Such modifications and variations are intended to fall within the scope of the claims which follow.

We claim:

1. A method for delivering oligonucleotide-stabilized lactone forms of camptothecin drugs to a host comprising the steps of: providing an oligonucleotide-camptothecin drug complex as a delivery vehicle wherein said camptothecin drug contains at least one lactone ring, and said oligonucleotide is RNA or catalytic RNA capable of associating with said camptothecin drug so that at least some part of the lactone ring is covalently tethered to said oligonucleotide and thereby protected from hydrolysis; and administering the oligonucleotide-camptothecin drug complex to the host.

2. A method of treating a patient with a chemotherapeutic composition, comprising:
    administering an oligonucleotide-camptothecin drug complex which incorporates sufficient amounts of active lactone camptothecin drug to exert therapeutic activity when administered to the body, wherein at least a part of the camptothecin drug lactone ring is covalently tethered to said oligonucleotide and thereby protected from hydrolysis during administration, and wherein the camptothecin drug dissociates from the oligonucleotide within the body and exerts its therapeutic activities.

3. The method of claim 2, wherein the camptothecin drug is selected from a group consisting of camptothecin; 10-hydroxycamptothecin; topotecan; 9-aminocamptothecin; 9-nitrocamptothecin; 10-hydroxycamptothecin; 10,11-methylenedioxycamptothecin; 9-nitro-10,11-methylenedioxy-camptothecin; 9-chloro-10,11-methylenedioxycamptothecin; 9-amino-10,11-methylenedioxycamptothecin; 7-ethyl-10-hydroxycamptothecin (SN-38); DX-8951; GG211; 7-trimethylsilylmethylcamptothecin; and mixtures thereof.

4. The method of claim 2, wherein the oligonucleotide is selected from the group consisting of single-stranded DNA, double-stranded DNA, antisense DNA, RNA, and catalytic RNA.

5. The method of claim 2, wherein said oligonucleotide-camptothecin drug complex is held within macromolecular assemblies of non-viral oligonucleotide vectors having a non-viral gene delivery system including transfection vehicles, naked DNA for injection, gene gun particles, liposomes including cationic liposomes, virosomes, receptor-mediated delivery vehicles, and biodegradable and non-biodegradable polymer matrixes.

6. The method of claim 2, further including lipid so as to form a lipid:oligonucleotide-camptothecin drug complex from a surfactant, lipid or mixture thereof, said lipid defining a compartment wherein said oligonucleotide-camptothecin drug complex exists and the camptothecin drug is held and protected from hydrolysis and is thus stabilized.

7. A chemotherapeutic composition, comprising an oligonucleotide-camptothecin drug complex including a pharmaceutically effective amount of active lactone camptothecin drug whereby at least a part of the camptothecin drug lactone ring is covalently tethered to said oligonucleotide and thereby protected from hydrolysis during administration, and wherein the camptothecin drug dissociates from the oligonucleotide within the body and exerts therapeutic activity.

8. The chemical composition of claim 7, wherein the camptothecin drug is selected from a group consisting of camptothecin; 10-hydroxycamptothecin; topotecan; 9-aminocamptothecin; 9-nitrocamptothecin; 10-hydroxycamptothecin; 10,11-methylenedioxycamptothecin; 9-nitro-10,11-methylenedioxy-camptothecin; 9-chloro-10,11-methylenedioxycamptothecin; 9-amino-10,11-methylenedioxycamptothecin; 7-ethyl-10-hydroxycamptothecin (SN-38); DX-8951; GG211; 7-trimethylsilylmethylcamptothecin; and mixtures thereof.

9. The composition of claim 7 wherein the oligonucleotide is selected from the group consisting of single-stranded DNA, double-stranded DNA, antisense DNA, RNA and catalytic RNA.

10. The composition of claim 7, wherein said oligonucleotide-camptothecin drug complex is held within macromolecular assemblies of non-viral oligonucleotide vectors having a non-viral gene delivery system including transfection vehicles, naked DNA for injection, gene gun particles, liposomes including cationic liposomes, virosomes, receptor-mediated delivery vehicles, and biodegradable and non-biodegradable polymer matrixes.

11. The composition of claim 7 further including lipid so as to form a lipid:oligonucleotide-camptothecin drug complex from a surfactant, lipid or mixture thereof, said lipid defining a compartment wherein said oligonucleotide-camptothecin drug complex exists and the camptothecin drug is held and protected from hydrolysis and is thus stabilized.

* * * * *